United States Patent
Michelson

(10) Patent No.: US 9,724,338 B2
(45) Date of Patent: Aug. 8, 2017

(54) METHODS OF USING (+)-1,4-DIHYDRO-7-[(3S,4S)-3-METHOXY-4-(METHYLAMINO)-1-PYRROLIDINYL]-4-OXO-1-(2-THIAZOLYL)-1,8-NAPHTHYRIDINE-3-CARBOXYLIC ACID FOR TREATMENT OF ANTECEDENT HEMATOLOGIC DISORDERS

(71) Applicant: SUNESIS PHARMACEUTICALS, INC., South San Francisco, CA (US)

(72) Inventor: Glenn Michelson, San Francisco, CA (US)

(73) Assignee: Sunesis Pharmaceuticals, Inc., South San Francisco, CA (US)

(*) Notice: Subject to any disclaimer, the term of this patent is extended or adjusted under 35 U.S.C. 154(b) by 0 days.

(21) Appl. No.: 14/517,535

(22) Filed: Oct. 17, 2014

(65) Prior Publication Data

US 2015/0250775 A1    Sep. 10, 2015

Related U.S. Application Data

(63) Continuation of application No. 13/477,963, filed on May 22, 2012, now abandoned, which is a continuation of application No. 12/747,167, filed as application No. PCT/US2008/013549 on Dec. 10, 2008, now abandoned.

(60) Provisional application No. 61/007,229, filed on Dec. 10, 2007.

(51) Int. Cl.

| | |
|---|---|
| *A61K 31/4375* | (2006.01) |
| *A61K 31/7068* | (2006.01) |
| *A61K 31/513* | (2006.01) |
| *A61K 45/06* | (2006.01) |
| *C07D 471/04* | (2006.01) |
| *A61K 31/706* | (2006.01) |
| *A61K 38/18* | (2006.01) |
| *A61K 38/19* | (2006.01) |
| *A61K 39/395* | (2006.01) |
| *A61K 39/00* | (2006.01) |

(52) U.S. Cl.
CPC ........ *A61K 31/4375* (2013.01); *A61K 31/513* (2013.01); *A61K 31/706* (2013.01); *A61K 31/7068* (2013.01); *A61K 38/18* (2013.01); *A61K 38/19* (2013.01); *A61K 39/39558* (2013.01); *A61K 45/06* (2013.01); *C07D 471/04* (2013.01); *A61K 2039/505* (2013.01); *A61K 2039/54* (2013.01)

(58) Field of Classification Search
None
See application file for complete search history.

(56) References Cited

U.S. PATENT DOCUMENTS

| | | | |
|---|---|---|---|
| 4,810,643 | A | 3/1989 | Souza |
| 4,999,291 | A | 3/1991 | Souza |
| 5,229,496 | A | 7/1993 | Deeley et al. |
| 5,391,485 | A | 2/1995 | Deeley et al. |
| 5,393,870 | A | 2/1995 | Deeley et al. |
| 5,528,823 | A | 6/1996 | Rudy, Jr. et al. |
| 5,580,755 | A | 12/1996 | Souza |
| 5,817,669 | A | 10/1998 | Tomita et al. |
| 7,829,577 | B2 | 11/2010 | Higaki et al. |
| 7,968,565 | B2 | 6/2011 | Arkin et al. |
| 7,989,468 | B2 | 8/2011 | Adelman et al. |
| 8,124,773 | B2 | 2/2012 | Adelman et al. |
| 8,138,202 | B2 | 3/2012 | Sudhakar et al. |
| 2005/0215583 | A1* | 9/2005 | Arkin ............ A61K 9/0019 514/300 |
| 2008/0063642 | A1 | 3/2008 | Adelman et al. |
| 2009/0263393 | A1 | 10/2009 | Adelman et al. |
| 2010/0048609 | A1 | 2/2010 | Jacobs |
| 2010/0203162 | A1 | 8/2010 | Sudhakar et al. |
| 2010/0297142 | A1 | 11/2010 | Silverman |
| 2011/0008371 | A1 | 1/2011 | Michelson |
| 2011/0082169 | A1 | 4/2011 | Sudhakar et al. |
| 2011/0105497 | A1 | 5/2011 | Sudhakar |
| 2012/0238598 | A1 | 9/2012 | Alam et al. |

FOREIGN PATENT DOCUMENTS

| | | |
|---|---|---|
| JP | Hei 10-173986 | 6/1998 |
| WO | 2004/034962 | 4/2004 |
| WO | 2004/043461 | 5/2004 |
| WO | 2007/076092 | 7/2007 |

OTHER PUBLICATIONS

Kaminskas et al. Approval summary: azacitidine for treatment of myelodysplastic syndrome subtypes. Clin. Cancer Res. 2005; 11: 3604-3608.*

Weihrauch et al. Phase I/II clinical study of topotecan and cytarabine in patients with myelodysplastic syndrome, chronic myelomonocytic leukemia and acute myeloid leukemia. Leukemia & Lymphoma, Apr. 2004, vol. 45(4), pp. 699-704.*

Arbitrario et al., "SNS-595 A Novel S-Phase Active Cytotoxic Acts Synergistically With Cytarabine to Reduce Bone Marrow Cellularity and Circulating Neutrophils," ASH Annual Meeting, 2006.

Bennett et al., "Proposals for the classification of the myelodysplastic syndromes," Br. J. Haematol. 51(2):189-199 (1982).

(Continued)

*Primary Examiner* — Anna Pagonakis
(74) *Attorney, Agent, or Firm* — Jones Day

(57) ABSTRACT

Methods of treating, preventing or managing antecedent hematologic disorders, such as myelodysplastic syndrome, including chronic myelomonocytic leukemia are disclosed. The methods encompass the administration of SNS-595. Also provided are methods of treatment using this compound with chemotherapy, radiation therapy, hormonal therapy, biological therapy or immunotherapy. In certain embodiments, the method of treatment comprise administering SNS-595 in combination with cytarabine. Pharmaceutical compositions and single unit dosage forms suitable for use in the methods are also disclosed.

6 Claims, No Drawings

(56) References Cited

OTHER PUBLICATIONS

Bennett et al., "The chronic myeloid leukaemias: guidelines for distinguishing chronic granulocytic, atypical chronic myeloid, and chronic myelomonocytic leukaemia. Proposals by the French-American-British Cooperative Leukaemia Group," Br. J. Haematol. 87(4):746-754 (1994).

Besa et al., "Erythroid response of severly anemic or transfusion-dependent patients with myelodysplastic syndrome to recombinant human erythropoietin (EPO) does not correlate with baseline serum EPO levels," Blood 76 (Suppl.1):133a (1990).

Besa, "Myelodysplastic Syndromes (Refractory Anemia). A perspective of the Biologic, Clinical, and Therapeutic Issues," Med. Clin. North Amer. 76(3): 599-617 (1992).

Bowen et al., "The treatment of anaemia in the myelodysplastic syndromes with recombinant human erythropoietin," Br. J. Haematol. 77(3):419-423 (1991).

Brunning et al., "Pathology and Genetics of Haematopoietic and Lymphoid Tissues," Lyon: IARC Press: 61-73 (2001).

Dexter, "Growth factors involved in haemopoiesis," J. Cell Sci. 88:1-6 (1987).

Dexter, "Haemopoietic growth factors," Br. Med. Bull. 45(2):337-349 (1989).

Emens et al., "Chemotherapy: Friend or foe to cancer vaccines?" Curr. Opinion Mol. Ther. 3(1):77-84 (2001).

Falini, "New Classification of Acute Myeloid Leukemia and Precursor-related Neoplasms: Changes and Unsolved Issues," Discov. Med. 10(53):281-292 (2010).

Foucar, "Myelodysplastic/Myeloproliferative Neoplasms," Am. J. Clin. Pathol. 132:281-289 (2009).

Goldberg et al., "Survey of Exposure to Genotoxic Agents in Primary Myelodysplastic Syndrome: Correlation with Chromosome Patterns and Data on Patients without Hematological Disease," Cancer Res. 50(21):6876-6881 (1990).

Golde and Gasson, "Hormones that Stimulate the Growth of Blood Cells," Scientific American 62-70 (1988).

Greenberg et al., "Erratum," Blood 91:1100 (1998).

Greenberg et al., "International Scoring System for Evaluating Prognosis in Myelodysplastic Syndromes" Blood 89 (6):2079-2088 (1997).

Handman and Burgess, "Stimulation by granulocyte-macrophage colony-stimulating factor of Leishmania tropica killing by macrophages," J. Immunol. 122(3):1134-1137 (1979).

Harris et al., "World Health Organization classification of neoplastic diseases of the hematopoietic and lymphoid tissues: report of the Clinical Advisory Committee meeting—Airlie House, Virginia, Nov. 1997," J. Clin. Oncol. 17(12):3835-3849 (1999).

Head, "A mechanistic pathogenetic model of myelodysplastic syndrome (MDS), separating MDS into 2 groups of disease," Hypotheses in the Life Sciences 1(2):38-45 (2011).

Hellström et al., "Treatment of myelodysplastic syndromes with recombinant human erythropoietin," Blood Abstract 1106, 76 (Suppl.1):279a (1990).

Hellström-Lindberg et al., "Achievements in Understanding and Treatment of Myelodysplastic Syndromes," Hematology 110-132 (2000).

Kurland et al., "Induction of prostaglandin E synthesis in normal and neoplastic macrophages: role for colony-stimulating factor(s) distinct from effects on myeloid progenitor cell proliferation," Proc. Natl. Acad. Sci. U.S.A. 76(5):2326-2330 (1979).

Lawrence et al., SNS-595, A Novel S-phase Active Cytotoxic, Exhibits Potent in Vitro and in Vivo Activities, and has the Potential for Treating Advanced Hematologic Malignancies, 97th Annual AACR Meeting 2006, Abstract No. 4726.

List et al., "The myelodysplastic syndromes: biology and implications for management," J. Clin. Oncol. 8(8):1424-1441 (1990).

Metcalf, "The granulocyte-macrophage colony-stimulating factors," Science 229(4708):16-22 (1985).

Mills et al., "SNS-595, a naphthyridine cell cycle inhibitor and stimulator of apoptosis for the treatment of cancers," Current Opinion in Investigational Drugs 9(6):647-657 (2008).

Moore et al., "Production of lymphocyte-activating factor (Interleukin 1) by macrophages activated with colony-stimulating factors," J. Immunol. 125(3):1302-1305 (1980).

Moore, "The clinical use of colony stimulating factors," Annu. Rev. Immunol. 9:159-191 (1991).

Ogawa, "Hemopoietic stem cells: stochastic differentiation and humoral control of proliferation," Environ. Health Presp. 80:199-207 (1989).

Schrader et al., "The persisting (P) cell: histamine content, regulation by a T cell-derived factor, origin from a bone marrow precursor, and relationship to mast cells," Proc. Natl. Acad. Sci. U.S.A. 78(1):323-327 (1981).

Stanley et al., "Factors regulating macrophage production and growth: identity of colony-stimulating factor and macrophage growth factor," J. Exp. Med. 143(3):631-647 (1976).

Tabarra and Robinson, "Hematopoietic growth factors," Anticancer Res. 11(1):81-90 (1991).

Tsuzuki, et al., "Practical Synthesis of (3S,4S)-3-Methoxy-4-Methylaminopyrrolidine." Tetrahedron: Asymmetry 12 (2001) 2989-2997.

Tsuzuki, et al., "Process Research of a Novel Quinolone Antitumor Agent, AG-7352." English Abstract, The Japanese Society for Process Chemstry, 2004 Summer Symposium.

Tsuzuki, et al., "Synthesis and Structure—Activity Relationships of 3-Substituted 1, 4-Dihydro-4-Oxo-1-(2-Thiazolyl)-1, 8-Naphthridines as Novel Antitumor Agents." Bioorganic & Medicinal Chemistry Letters 14 (2004): 3189-3193.

Tsuzuki, et al., "Synthesis and Structure—Activity Relationships of Novel 7-Substituted 1.4-Dihydro-4-Oxo-1-(2-Thiazolyl)-1.8-Naphthyridine-3-Carboxylic Acids as Antitumor Agents. Part 2." J. Med. Chem. 2004, 47: 2097-2109.

Vadas et al., "Activation of antibody-dependent cell-mediated cytotoxicity of human neutrophils and eosinophils by separate colony-stimulating factors," J. Immunol. 130(2):795-799 (1983).

Vadas et al., "Eosinophil activation by colony-stimulating factor in man: metabolic effects and analysis by flow cytometry," Blood 61(6):1232-1241 (1983).

Vardiman et al., "The World Health Organization (WHO) classification of the myeloid neoplasms," Blood 100(7):2292-2302 (2002).

Vardiman et al., "The 2008 revision of the World Health Organization (WHO) classification of myeloid neoplasms and acute leukemia: rationale and important changes," Blood 114(5):937-951 (2009). (Epub Apr. 8, 2009).

Weisbart et al., "Biosynthetic human GM-CSF modulates the number and affinity of neutrophil f-Met-Leu-Phe receptors," J. Immunol. 137(11):3584-3587 (1986).

Kaminskas et al., "Approval Summary: Azacitidine for Treatment of Myelodysplastic Syndrome Subtypes," Clin. Cancer Res., 11:3604-3608 (2005).

Jacoby et al., "A phase I study of vosaroxin plus azacitidine for patients with myelodysplastic syndrome," American Society of Hematology, 57th Annual Meeting & Exposition, Dec. 5, 2015, Abstract 1686.

Jacobson, "Combination regimens show no advantage over azacitidine monotherapy in high-risk MDS," The Oncologist, [online], The Oncologist, vol. 19, Issue No. 12, Dec. 2014, [retrieved on Dec. 14, 2016]. Retrieved from the internet <URL:http://theoncologist.alphamedpress.org/site/misc/ASH2014_D4A2.xhtml>, 1 page.

Sekeres et al., A randomized phase ii study of azacitidine combined with lenalidomide or with vorinostat vs. azacitidine monotherapy in higher-risk myelodysplastic syndromes (MDS) and chronic myelomonocytic leukemia (CMML): North American Intergroup Study SWOG S1117, [online], Blood 124:LBA-5 (2014), [retrieved on Dec. 14, 2016]. Retrieved from the internet <YRL:http://www.bloodjournal.org/content/124/21/LBA-5>, 6 pages.

Kaminskas et al., FDA Drug Approval Summary: Azacitidine (5-azacytidine, Vidaza™) for Injectable Suspension, The Oncologist, 2005, 10, pp. 176-183.

(56) References Cited

OTHER PUBLICATIONS

Quintas-Cardama et al., Activity of 9-Nitro-camptothecin, an Oral Topoisomerase I Inhibitor, in Myelodysplastic Syndrome and Chronic Myelomonocytic Leukemia, Cancer, 2006, 107(7), pp. 1525-1529.

* cited by examiner

METHODS OF USING (+)-1,4-DIHYDRO-7-[(3S,4S)-3-METHOXY-4-(METHYLAMINO)-1-PYRROLIDINYL]-4-OXO-1-(2-THIAZOLYL)-1,8-NAPHTHYRIDINE-3-CARBOXYLIC ACID FOR TREATMENT OF ANTECEDENT HEMATOLOGIC DISORDERS

1. RELATED APPLICATIONS

This application is continuation application of U.S. application Ser. No. 13/477,963, filed May 22, 2012, which is continuation application of U.S. application Ser. No. 12/747,167, filed Sep. 9, 2010, which is a National stage under 35 U.S.C. §371 of International Application No. PCT/US2008/013549, filed Dec. 10, 2008, which claims priority to U.S. provisional application No. 61/007,229, filed Dec. 10, 2007. The disclosures of the above referenced applications are incorporated by reference herein in their entireties.

2. FIELD OF THE INVENTION

Provided herein are methods of treating, preventing or managing antecedent hematologic disorders, including myelodysplastic syndrome, with enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, which is also known as SNS-595 or AG-7352.

Further provided is a combination therapy for treatment of antecedent hematologic disorders comprising administering a combination of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and cytarabine (Ara-C). Also provided are pharmaceutical compositions and dosing regimens for the methods provided herein.

3. BACKGROUND OF THE INVENTION

Antecedent hematological disorders include the disorders myelofibrosis, aplastic anemia, paroxysmal nocturnal hemoglobinuria, polycythemia vera, and most commonly myelodysplastic syndrome. Myelodysplastic syndrome (MDS) refers to hematological conditions characterized by abnormalities in the production of one or more of the cellular components of blood (red cells, white cells (other than lymphocytes) and platelets (or their progenitor cells, megakaryocytes). MDS possesses a variable risk of progression to acute leukemia, resulting from ineffective blood cell production. The Merck Manual 953 (17th ed. 1999) and List et al., 1990, *J. Clin. Oncol.* 8:1424. Myelodysplastic syndromes (MDS) may be classified into several subtypes according to various systems of classification.

According to the French-American-British classification system, MDS may be classified according to the respective percentages of peripheral blasts and bone marrow blasts of the patient. See e.g., Bennett et al., *Br. J. Haematol.* 51:189-199 (1982); and Bennett et al., *Br. J. Haematol.* 87:746-754 (1994). Patients with MDS are classified as having one of five subtypes of disease: refractory anemia (RA); RA with ringed sideroblasts (RARS); RA with excess of blasts (RAEB); RAEB in transformation (RAEB-T); and chronic myelomonocytic leukemia (CMML). Myelodysplastic syndromes are generally indolent, with patients' blood counts remaining relatively stable over at least several months. With a moderate degree of variability, RAEB patients (those with 5% to 20% marrow blasts) and those with RAEB-T (20% to 30% marrow blasts) generally have a relatively poor prognosis, with a median survival ranging from 5 to 12 months. In contrast, RA patients (fewer than 5% blasts) or RARS patients (fewer than 5% blasts plus more than 15% ringed sideroblasts) have a median survival of approximately 3 to 6 years. The proportion of these individuals whose disease transforms to AML ranges from 5% to 15% in the low-risk RA/RARS group to 40% to 50% in the relatively high-risk RAEB/RAEB-T group. The FAB classification categorizes patients with more than 30% marrow blasts as having AML.

The subtype CMML can have 5-20% bone marrow blasts with a monocytosis of 1000/dL or more. It may be associated with splenomegaly. This subtype overlaps with a myeloproliferative disorder and may have an intermediate clinical course. It is differentiated from the classic chronic myelocytic leukemia (CML) that is characterized by a negative Ph chromosome.

MDS can also be classified according to the World Health Organization's (WHO) proposed system of classification. See, e.g. Brunning et al., *Pathology and Genetics of Haematopoietic and Lymphoid Tissues*, Lyon: IARC Press: 61-73 (2001); Harris et al., *J. Clin. Oncol.* 17:3835-3849 (1999); and Vardiman et al., *Blood* 100:2292-2302 (2002). MDS can be categorized under the WHO classification system according to the following criteria:

Refractory anemia (RA) is characterized by anemia with no or few blasts in the blood, and bone marrow displaying erythroid dysplasia only, less than 5% blasts, and less than 15% ringed sideroblasts.

Refractory cytopenia with multilineage dysplasia (RCMD) is characterized by cytopenias with no or few blasts in the blood, and bone marrow displaying dysplasia in greater than at least 10% of cells in at least 2 myeloid cell lines, less than 5% blasts, at least 15% ringed sideroblasts, and no Auer rods.

Refractory anemia with ringed sideroblasts (RARS) is characterized by anemia with no or rare blasts in the blood, and bone marrow displaying erythroid dysplasia only, less than 5% blasts, and at least 15% ringed sideroblasts.

Refractory cytopenia with multilineage dysplasia and ringed sideroblasts (RCMD-RS) is characterized by cytopenias with no or few blasts in the blood, and bone marrow displaying dysplasia at least 10% of cells in at least two myeloid cell lines, less than 5% blasts, no Auer rods, and at least 15% ringed sideroblasts.

Refractory anemia with excess blasts-1 (RAEB-1) is characterized by cytopenias with less than 5% blasts in the blood with no Auer rods, and bone marrow displaying unilineage or multilineage dysplasia, 5% to 9% blasts, and no Auer rods.

Refractory anemia with excess blasts-2 (RAEB-2) is characterized by cytopenias with between 5-19% blasts in the blood, and bone marrow displaying unilineage or multilineage dysplasia, and 10% to 19% blasts.

Myelodysplastic Syndrome, unclassified (MDS-U), is characterized by cytopenias with no or rare blasts in the blood and no Auer rods, and bone marrow displaying unilineage dysplasia in granulocytes or megakaryocytes, less than 5% blasts, and no Auer rods.

MDS associated with isolated del (5q) is characterized by anemia with less than 5% blasts in blood with normal or increased platelets, and bone marrow displaying normal or increased megakaryocytes with hypoloblated nuclei, less than 5% blasts, no Auer rods, and an isolated 5q31-33 chromosomal deletion.

MDS can also be classified according to the International Prognostic Scoring System. See, e.g. Greenberg et al., *Blood* 89:2079-2088 (1997); and Greenberg et al., *Blood* 91:1100 (1998). Under IPSS scoring, prognostic values are assigned to 3 categories: (1) percent marrow blasts (less than 5%=0;

5-10%=0.5; 11-20%=1.0; and 21-30%=2.0); (2) karyotype (normal cytogenetics=0; some chromosomal defects=0.5; complex, or chromosome 7 anomalies=1.5); and (3) cytopenia (a score of 0 if one of the following criteria are met: neutrophil count<1,800/mcL, platelets<100,000/mcL, Hb<10 g/dL; a score of 0.5 if two of three criteria are met). Risk is then determined based on the cumulative score of the 3 categories: "low" risk of MDS for an overall score of 0; "INT-1" risk of MDS for a score of 0.5-1; "INT-2" risk of MDS for an overall score of 1.5-2.0; and "high" risk of MDS for an overall score of 2.5 or higher.

The most common cases of MDS are primary, or idiopathic. However, a nonspecific history of exposure to indeterminable chemicals or radiation 10-15 years prior to onset of disease may be present in about 50% of patients. This relationship to pathogenesis remains unproved. Compounds such as, but not limited to, benzene, insecticides, weed killers, and fungicides are possible causes of MDS. Goldberg H., et al., Cancer Res. 1990 Nov. 1; 50(21): 6876-81. Secondary MDS describes development of MDS or acute leukemia after known exposures to chemotherapy drugs that can cause bone marrow damage. These drugs are associated with a high incidence of chromosomal abnormalities following exposure and at the time of MDS or acute leukemia diagnosis.

Further, MDS is associated with complications associated with severe cytopenias. Other complications are development of myelofibrosis, which can accelerate decline in blood counts and increase transfusion requirements. Transformation to acute leukemia accelerates the development of complications such as anemia, bleeding, and infections.

MDS Treatments

The current treatment of MDS is based on the stage and the mechanism of the disease that predominates the particular phase of the disease process. Bone marrow transplantation has been used in patients with poor prognosis or late-stage MDS. Epstein and Slease, 1985, Surg. Ann. 17:125. This type of therapy, however, is both painful for donor and recipient, because of the involvement of invasive procedures and can cause severe and even fatal complications to the recipient, particularly with allogeneic transplant and related Graft Versus Host Disease (GvHD) results. Therefore, the risk of GvHD restricts the use of bone marrow transplantation to patients with otherwise fatal diseases. Further, as most patients are elderly and only a few young MDS patients will have a matched donor, the use of bone marrow transplantation is limited.

An alternative approach to therapy for MDS is the use of hematopoietic growth factors or cytokines to stimulate blood cell development in a recipient. Dexter, 1987, J. Cell Sci. 88:1; Moore, 1991, Annu. Rev. Immunol. 9:159; and Besa E. C., Med. Clin. North Amer. 1992 May, 76(3): 599-617. The process of blood cell formation, by which a small number of self-renewing stem cells give rise to lineage specific progenitor cells that subsequently undergo proliferation and differentiation to produce the mature circulating blood cells has been shown to be at least in part regulated by specific hormones. These hormones are collectively known as hematopoietic growth factors. Metcalf, 1985, Science 229: 16; Dexter, 1987, J. Cell Sci. 88:1; Golde and Gasson, 1988, Scientific American, July: 62; Tabbara and Robinson, 1991, Anti-Cancer Res. 11:81; Ogawa, 1989, Environ. Health Presp. 80:199; and Dexter, 1989, Br. Med. Bull. 45:337. The most well characterized growth factors include erythropoietin (EPO), granulocyte macrophage colony stimulating factor (GM-CSF), and granulocyte colony stimulating factor (G-CSF). Apart from inducing proliferation and differentiation of hematopoietic progenitor cells, such cytokines have also been shown to activate a number of functions of mature blood cells, including influencing the migration of mature hematopoietic cells. Stanley et al., 1976, J. Exp. Med. 143:631; Schrader et al., 1981, Proc. Natl. Acad. Sci. U.S.A. 78:323; Moore et al., 1980, J. Immunol. 125:1302; Kurland et al., 1979, Proc. Natl. Acad. Sci. U.S.A. 76:2326; Handman and Burgess, 1979, J. Immunol. 122:1134; Vadas et al., 1983, Blood 61:1232; Vadas et al., 1983, J. Immunol. 130:795; and Weibart et al., 1986, J. Immunol. 137:3584.

Unfortunately, hematopoietic growth factors have not proven effective in many clinical settings. Clinical trials of MDS patients treated with recombinant human GM-CSF and G-CSF have shown that while these cytokines can restore granulocytopoiesis in treated patients, their efficacy is restricted to the granulocyte or monocyte lineage with little or no improvement in hemoglobin or platelet counts. Schuster et al., 1990, Blood 76 (Suppl. 1):318a. When such patients were treated with recombinant human EPO, a sustained improvement in hemoglobin or decrease in transfusion requirement was achieved in only less than 25% of patients. Besa et al., 1990, Blood, 76 (Suppl. 1):133a; Hellstrom et al., 1990, Blood, 76 (Suppl. 1):279a; Bowen et al., 1991, Br. J. Haematol. 77:419.

Therefore, there remains a need for safe and effective methods of treating and managing antecedent hematological disorders, including MDS.

4. SUMMARY OF THE INVENTION

Provided herein are methods of treating, preventing or managing antecedent hematological disorders, including myelofibrosis, aplastic anemia, paroxysmal nocturnal hemoglobinuria, polycythemia vera, and myelodysplastic syndrome. In one embodiment, methods are for treating, preventing or managing myelodysplastic syndrome (MDS), including CMML. In certain embodiments, provided herein are methods for treating, preventing or managing CMML.

The methods comprise administering to a subject in need of such treatment, prevention or management a therapeutically or prophylactically effective amount of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid. In some embodiments, (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is used alone, e.g., without other chemotherapeutics.

In another embodiment, (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is administered in combination with a therapy, e.g., another pharmaceutical agent with activity against cancer or its symptoms. Examples of therapies within the scope of the methods include, but are not limited to, surgery, chemotherapy, radiation therapy, hormonal therapy, biological therapy, immunotherapy, and combinations thereof. It should be noted that the combinations encompass simultaneous as well as sequential administration.

In a particular embodiment, the combination therapy comprises administering (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and cytarabine.

Also provided are dosing regimens, dosing schedules and methods of using SNS-595 in combination with cytarabine.

The methods provided include the administration of SNS-595 in combination with 5-1500 mg/m$^2$ of cytarabine. For example, one embodiment includes continuous daily administration of cytarabine at a dose of 200-400 mg/m². The administration of cytarabine can be made by intravenous infusion, intravenous push, bolus injection or subcutaneous injection. In one embodiment, the administration of cytarabine is daily, e.g., for 5 days, while the administration of SNS-595 occurs once or twice per week. As discussed herein, the administration of SNS-595 and cytarabine as set forth above in a week is considered a weekly cycle. The methods contemplate performing one weekly cycle, waiting a period of one week to several weeks where neither cytarabine nor SNS-595 is given, then repeating a weekly cycle. The methods also contemplate repeating the weekly cycles continuously, for example, for 4 weeks or 28 days. In addition, the methods contemplate repeating the cycle for several cycles, waiting a period of a week to several weeks where neither cytarabine nor SNS-595 is given, then repeating one or more cycles. Finally, the methods provide administration of a SNS-595/cytarabine weekly cycle followed by a cycle of only cytarabine or SNS-595.

Also provided are methods where the daily cytarabine administration is at a dose of 5-50 mg/m² and where the SNS-595 is administered once a week or twice a week. For example, cytarabine may be administered daily for 10 days, and SNS-595 may be administered on a schedule of once a week for three weeks, or twice a week for two weeks.

Also provided are pharmaceutical compositions, single unit dosage forms, and dosing regimens which comprise (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, and a second, or additional, active agent. Second active agents include specific drugs or therapy, or combinations thereof, i.e. "cocktails."

5. DETAILED DESCRIPTION OF THE INVENTION

Provided herein are methods of treating, managing, or preventing antecedent hematologic disorders comprising administering to a mammal in need of such treatment, management or prevention a therapeutically or prophylactically effective amount of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid alone, or in combination with another chemotherapeutic agent such as cytarabine. In one embodiment, the methods encompass treating, preventing or managing antecedent hematological disorders (AHD). In one embodiment, the antecedent hematological disorder is CMML.

In other embodiments, (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is administered in combination with another drug (i.e. a "second active agent") or another therapy for treating, managing, or preventing cancer. Second active agents include small molecules and large molecules (e.g., proteins and antibodies), examples of which are provided herein, as well as stem cells or cord blood. Methods or therapies that can be used in combination with the administration of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid include, but are not limited to, surgery, blood transfusions, immunotherapy, biological therapy, radiation therapy, and other non-drug based therapies presently used to treat, prevent or manage cancer.

In one embodiment, the combination therapy comprises administering (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and cytarabine. Specific doses and dosing regimens for the combination therapy are provided below.

Also provided are pharmaceutical compositions (e.g., single unit dosage forms) that can be used in methods disclosed herein. In one embodiment, pharmaceutical compositions comprise (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and a second active agent.

Definitions

Unless defined otherwise, all technical and scientific terms used herein have the same meaning as is commonly understood by one of ordinary skill in the art. All patents, applications, published applications and other publications are incorporated by reference in their entirety. If there are a plurality of definitions for a term herein, those in this section prevail unless stated otherwise.

As used herein, enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is substantially free from (−)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (i.e., in enantiomeric excess). In other words, the "(+)" form of 1,4-dihydro-7-[(3S,4S)-3-methoxy-4-(methylamino)-1-pyrrolidinyl]-4-oxo-1-(2-thiazolyl)-1,8-naphthyridine-3-carboxylic acid is substantially free from the "(−)" form of the compound and is, thus, in enantiomeric excess of the "(−)" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, or more than 97% by weight of the enantiomer.

As used herein and unless otherwise indicated, the term "enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid" refers to at least about 80% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 20% by weight (−)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, at least about 90% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 10% by weight the (−)-enantiomer, at least about 95% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 5% by weight the (−)-enantiomer, at least about 97% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 3% by weight (−)-enantiomer.

As used herein, administration of (+)-1,4-dihydro-7-[(3S,4S)-3-methoxy-4-methylamino-1-pyrrolidinyl]-4-oxo-1-(2-thiazolyl)-1,8-naphthyridine-3-carboxylic acid includes administration of (+)-1,4-dihydro-7-[(3S,4S)-3-methoxy-4-methylamino-1-pyrrolidinyl]-4-oxo-1-(2-thiazolyl)-1,8-naphthyridine-3-carboxylic acid, as well as any ionic form, salts, solvates, e.g., hydrate, or other forms of that compound, including mixtures thereof. Thus, compositions comprising (+)-1,4-dihydro-7-[(3S,4S)-3-methoxy-4-methylamino-1-pyrrolidinyl]-4-oxo-1-(2-thiazolyl)-1,8-naphthyridine-3-carboxylic acid may include (+)-1,4- dihydro-7-[(3S,4S)-3-methoxy-4-methylamino-1-pyrrolidinyl]-4-oxo-1-(2-thiazolyl)-1,8-naphthyridine-3-carboxylic acid or an ionic form thereof, salt, solvate, e.g., hydrate, or other form of the compound.

As used herein, "subject" is an animal, typically a mammal, including a human, such as a human patient.

As used herein, the term "antecedent hematological disorders" includes the disorders myelofibrosis, aplastic anemia, paroxysmal nocturnal hemoglobinuria, polycythemia vera, and myelodysplastic syndrome.

The term "myelodysplastic syndrome" refers to hematological conditions characterized by abnormalities in the production of one or more of the cellular components of blood (red cells, white cells (other than lymphocytes) and platelets (or their progenitor cells, megakaryocytes), and include the following disorders: refractory anemia (RA); RA with ringed sideroblasts (RARS); RA with excess of blasts (RAEB); RAEB in transformation (RAEB-T); and CMML.

As used herein, "chronic myelomonocytic leukemia" or "CMML" refers to a clonal disorder of a bone marrow stem cell, wherein an abundance of myelocytes and monocytes (immature white blood cells) are made in the bone marrow resulting in the crowding out of normal blood cells, such as other white blood cells, red blood cells, and platelets. In certain embodiments, CMML is refractory to and/or relapsed from prior therapy.

As used herein and unless otherwise indicated, the terms "treat," "treating" and "treatment" refer to alleviating or reducing the severity of a symptom associated with the disease or condition being treated.

As used herein, unless otherwise specified, the term "preventing" includes but is not limited to, inhibition or the averting of symptoms associated with antecedent hematologic disorders, including MDS. The symptoms associated with antecedent hematologic disorder include, but are not limited to, anemia, thrombocytopenia, neutropenia, cytopenia, bicytopenia (two deficient cell lines), and pancytopenia (three deficient cell lines).

As used herein and unless otherwise indicated, the term "managing" encompasses preventing the recurrence of antecedent hematologic disorders, including MDS, in a patient who had suffered from antecedent hematologic disorders, lengthening the time a patient who had suffered from antecedent hematologic disorders remains in remission, and/or preventing the occurrence of antecedent hematologic disorders in patients at risk of suffering from antecedent hematologic disorders.

As used herein and unless otherwise indicated, the term "pharmaceutically acceptable salt" includes, but is not limited to, salts of acidic or basic groups that can be present in the compounds provided herein. Under certain acidic conditions, the compounds can form a variety of salts with various inorganic and organic acids. The acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide and pamoate. Under certain basic conditions, the compounds can form base salts with various pharmacologically acceptable cations. Non-limiting examples of such salts include alkali metal or alkaline earth metal salts and, particularly, calcium, magnesium, sodium, lithium, zinc, potassium and iron salts.

As used herein and unless otherwise indicated, the term "hydrate" means a compound provided herein, or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of two therapeutic agents (for example, SNS-595 and another anti-cancer agent) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

The term "the supportive care agent" refers to any substance that treats, prevents or manages an adverse effect associated with SNS-595 treatment.

The term "biological therapy" refers to administration of biological therapeutics such as cord blood, stem cells, growth factors and the like.

The term "about," as used herein, unless otherwise indicated, refers to a value that is no more than approximately 10% above or below the value being modified by the term.

SNS-595

The compound for use in the methods provided herein, including the combination therapy, and in compositions provided herein is enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, which is also known as SNS-595 or AG-7352. The name assigned by the United States Adopted Names Council (USANC) to the compound is "voreloxin". SNS-595 has the following chemical structure:

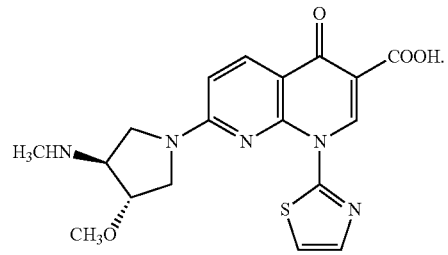

In certain embodiments, pharmaceutically acceptable salts, solvates, hydrates or prodrugs of SNS-595 are used in the methods and compositions provided herein.

SNS-595 can be prepared by methods known to one of skill in the art, for example, according to the preparation procedure for Example C-1 of U.S. Pat. No. 5,817,669, entitled "Compounds, processes for the preparation thereof and anti-tumor agents," issued Oct. 6, 1998, and in Japanese Patent Application No. Hei 10-173986, to Chikugi et al., which are incorporated herein by reference in their entireties. Certain exemplary pharmaceutical compositions comprising SNS-595 and methods of using the same are described in U.S. Patent Application Pub. Nos. 2005/0203120; 2005/0215583; 2006/0025437; 2006/0063795 and 2006/0247267, which are incorporated herein by reference in their entireties.

Second Active Agents

In the methods and compositions provided herein, SNS-595 can be used with or combined with other pharmacologically active compounds ("second active agents"). Without being limited by any theory, it is believed that certain combinations work synergistically in the treatment of particular antecedent hematologic disorders. The methods also encompass the use of SNS-595 in a manner to alleviate, reduce or avoid adverse effects associated with certain second active agents. Also provided are methods, wherein the second active agents are used in the manner to alleviate, reduce or avoid adverse or unwanted effects associated with SNS-595, including dose limiting toxicity.

One or more second active ingredients or agents can be used together with SNS-595 in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; G-CSF and GM-CSF; and EPO.

Also provided for use in combination with SNS-595 are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1- or IgG3-derived proteins to the protein of interest or an active portion thereof. See, e.g., Penichet, M. L. and Morrison, S. L., J. Immunol. Methods 248:91-101 (2001).

Antibodies that can be used in combination with SNS-595 include monoclonal and polyclonal antibodies. Examples of antibodies include, but are not limited to, trastuzumab (e.g., HERCEPTIN®), rituximab (e.g., RITUXAN®), bevacizumab (e.g., AVASTIN®), pertuzumab (e.g., OMNITARG®), tositumomab (e.g., BEXXAR®), edrecolomab (e.g., PANOREX®), CD20 antibodies such as ibritumomab tiuxetan (e.g., ZEVALIN®)+$^{111}$In or $^{90}$Yt or ofatumumab; CD23 antibodies such as lumiliximab; CD33 antibodies such as gemtuzumab ozogamicin(MYLOTARG®) or lintuzumab; CD52 antibodies such as alemtuzumab (e.g., CAMPATH®); CD80 antibodies such as galiximab; and G250. SNS-595 can also be combined with, or used in combination with, anti-TNF-α antibodies such as infliximab (e.g., REMICADE®) or adalimumab (e.g., HUMIRA®), anti-IL-2 antibodies such as daclizumab (dacliximab, e.g., ZENAPAX® HUMIRA®), and/or anti-EGFR antibodies, such as cetuximab (e.g., ERBITUX®) or panitumumab (e.g., VECTIBIX®).

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., Curr. Opinion Mol. Ther. 3(1):77-84 (2001).

Second active agents that are small molecules can also be used to alleviate adverse effects associated with the administration of SNS-595. However, like some large molecules, many are believed to be capable of providing a synergistic effect when administered with (e.g., before, after or simultaneously) SNS-595. Examples of small molecule second active agents include, but are not limited to, anti-cancer agents, antibiotics, immunosuppressive agents, and steroids. Examples of chemotherapeutic anticancer agents that may be used as second active agents in combination with SNS-595 include, but are not limited to, alkylating agents (e.g., mechlorethamine, chlorambucil, cyclophosphamide, melphalan, ifosfamide), antimetabolites (e.g., methotrexate), purine antagonists and pyrimidine antagonists (e.g., 6-mercaptopurine, 5-fluorouracil, cytarabine, capecitabine, decitabine, gemcitabine), spindle poisons (e.g., vinblastine, vincristine, vinorelbine, paclitaxel), podophyllotoxins (e.g., etoposide, irinotecan, topotecan), antibiotics (e.g., doxorubicin, daunorubicin, bleomycin, mitomycin), nitrosoureas (e.g., carmustine, lomustine), inorganic ions (e.g., platinum complexes such as cisplatin, carboplatin), enzymes (e.g., asparaginase), hormones (e.g., tamoxifen, leuprolide, flutamide, and megestrol), EGFR (Her1, ErbB-1) inhibitors (e.g., gefitinib), antibodies (e.g., rituximab), IMIDs (e.g., thalidomide, lenalidomide), various targeted agents (e.g., HDAC inhibitors such as vorinostat), Bcl-2 inhibitors, VEGF inhibitors); proteasome inhibitors (e.g., bortezomib) and dexamethasone.

Examples of anti-cancer agents to be used within the methods or compositions described herein include, but are not limited to: acivicin; aclarubicin; acodazole hydrochloride; acronine; adozelesin; alitretinoin (e.g., PANRETIN®); altretamine (hexamethylmelamine; e.g., HEXALEN®);); ambomycin; ametantrone acetate; aminoglutethimide (e.g., CYTADREN®); amonafide malate (e.g., XANAFIDE®); amsacrine; anastrozole (e.g., ARIMIDEX®); anthramycin; asparaginase (e.g., KIDROLASE®) ELSPAR®); asperlin; azacitidine (e.g., VIDAZA®); azetepa; azotomycin; batimastat; benzodepa; bexarotene (e.g., TARGETIN®); bicalutamide (e.g., CASODEX®); bisantrene hydrochloride; bisnafide dimesylate; bizelesin; bleomycin sulfate (e.g., BLENOXANE®); bortezomib (e.g., VELCADE®); brequinar sodium; bropirimine; busulfan (e.g., BUSULFEX®, MYLERAN®); cactinomycin; calusterone; capecitabine (e.g., XELODA®); caracemide; carbetimer; carmustine (e.g., BiCNU®); carmustine implant (e.g., GLIADEL® wafer); carubicin hydrochloride; carboplatin (e.g., PARAPLATIN®); carzelesin; cedefingol; celecoxib (COX-2 inhibitor, e.g., CELEBREX®); chlorambucil (e.g., LEUKERAN®); cirolemycin; cisplatin (e.g., PLATINOL®); cladribine (e.g., LEUSTATIN®); clofarabine; cloretazine; crisnatol, crisnatol mesylate; cyclophosphamide (e.g., CYTOXAN®, NEOSAR®); 4-hydroperoxycyclophosphamide; dacarbazine (e.g., DTIC-DOME®); dactinomycin (e.g., COSMEGEN®); dasatanib (e.g., SPRYCEL®); daunorubicin hydrochloride (e.g., CERUBIDINE®), liposomal daunorubicin citrate (e.g., DAUNOXOME®); decitabine (e.g., DACOGEN®); denileukin diftitox (e.g., ONTAK®); dexormaplatin; dezaguanine, dezaguanine mesylate; diaziquone; doxorubicin, doxorubicin hydrochloride (e.g., ADRIAMYCIN®), liposomal doxorubicin hydrochloride (e.g., DOXIL®); droloxifene, droloxifene citrate; dromostanolone propionate; duazomycin; edatrexate; eflornithine, eflornithine hydrochloride; elsamitrucin; enloplatin; enpromate; epipropidine; epirubicin hydrochloride (e.g., ELLENCE®); erbulozole; erlotinib (e.g., TARCEVA®); esorubicin hydrochloride; estramustine, estramustine phosphate sodium (e.g., EMCYT®), estramustine analogues; etanidazole; etoposide (VP-16; e.g., TOPOSAR®), etoposide phosphate (e.g., ETOPOPHOs®); etoprine; fadrozole hydrochloride; fazarabine; fenretinide; floxuridine (e.g., FUDR®); fludarabine, fludarabine phosphate (FLUDARA®); flurocitabine; 5-fluorouracil (e.g., ADRUCIL®; flutamide (e.g., EULEXIN®); fosquidone; fostriecin, fostriecin sodium; gefitinib (e.g., IRESSA®); gemcitabine hydrochloride (e.g., GEMZAR®); goserelin acetate (ZOLADEX®); hydroxyurea (e.g., DROXIA®, HYDREA®); idarubicin, idarubicin hydrochloride (e.g., IDAMYCIN®); ifosfamide (e.g., IFEX®); ilmofosine; iproplatin; irinotecan (CPT-11, camptothecin-11), irinotecan hydrochloride (e.g., CAMPTOSAR®); lanreotide, lanreotide acetate; lapatinib (e.g., TYKERB®); lenalidomide (e.g., REVLIMID®); letrozole (e.g., FEMARA®); leuprolide acetate (e.g., ELIGARD®, VIADUR®); liarozole, liarozole hydrochloride; lometrexol, lometrexol sodium; lomustine (e.g., CEENU®); losoxantrone, losoxantrone hydrochloride; masoprocol; maytansine; mechlorethamine (nitrogen mustard, mustine), mechlorethamine hydrochloride (e.g., MUSTARGEN®); megestrol acetate (e.g., MEGACE®); melengestrol acetate; melphalan (e.g., ALKERAN®); menogaril; mercaptopurine (e.g., PURINETHOL®); methotrexate sodium (e.g., RHEUMATREX®); metoprine; meturedepa; mitindomide; mitocarcin; mitocromin; mitogillin; mitomalcin; mitomycin (MUTAMYCIN®), mitomycin analogues; mitosper; mitotane; mitoxantrone, mitoxantrone hydrochloride (e.g., NOVANTRONE®); mycophenolic acid; nelarabine(ARRANON®); nocodazole; nogalamycin; ormaplatin; oxisuran; paclitaxel (e.g., TAXOL®); paclitaxel protein-bound (e.g., ABRAXANE®); pegaspargase (PEG-L-asparaginase; e.g., ONCASPAR®); peliomycin; pemetrexed (e.g., ALIMTA®); pentamustine; peplomycin sulfate; perfosfamide; pipobroman; piposulfan; pixoxantrone hydrochloride; plicamycin; plomestane; porfimer sodium; porfiromycin; prednimustine; procarbazine hydrochloride (e.g., MATULANE®); puromycin; puromycin hydrochloride; pyrazofurin; R-roscovitine (seliciclib); riboprine; safingol; safingol hydrochloride; semustine; simtrazene; sorafenib (e.g., NEXAVAR®); sparfosate sodium; sparsomycin; spirogermanium hydrochloride; spiromustine; spiroplatin; streptonigrin; streptozocin (e.g., ZANOSAR®); sulofenur; sunitinib malate (e.g., SUTENT®); talisomycin; tecogalan sodium; tegafur; teloxantrone hydrochloride; temoporfin; temozolomide (e.g., TEMODAR®); teniposide (e.g., VUMON®); teroxirone; testolactone; thalidomide (e.g., THALOMID®); thiamiprine; thioguanidine; 6-thioguanine; thiotepa (e.g., THIOPLEX®); tiazofurin; tipifarnib (e.g., ZARNESTRA®); tirapazamine; topotecan (e.g., HYCAMTIN®); toremifene, toremifene citrate (e.g., FARESTON®); trestolone acetate; triciribine, triciribine phosphate; trimetrexate, trimetrexate glucuronate; triptorelin; troxacitabine (e.g., TROXATYL®); tubulozole hydrochloride; uracil mustard; uredepa; vapreotide; verteporfin; vinblastine sulfate (e.g., VELBAN®); vincristine (leurocristine) sulfate (e.g., VINCASAR®); vindesine, vindesine sulfate; vinepidine sulfate; vinglycinate sulfate; vinleurosine sulfate; vinorelbine tartrate (e.g., NAVELBINE®); vinrosidine sulfate; vinzolidine sulfate; vorinostat (e.g., ZOLINZA®); vorozole; zeniplatin; zinostatin, zinostatin stimalamer; and zorubicin (rubidazone) hydrochloride.

Other anti-cancer drugs to be included within the methods or comprising include, but are not limited to: 20-epi-1,25-dihydroxyvitamin D3; 5-ethynyluracil; abiraterone acetate; acylfulvene, (hydroxymethyl)acylfulvene; adecypenol; ALL-TK antagonists; ambamustine; amidox; amifostine; aminolevulinic acid; amrubicin; anagrelide (e.g., AGRYLIN®); andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; arsenic trioxide (e.g., TRISENOX®); asulacrine; atamestane; atrimustine; axinastatin 1; axinastatin 2; axinastatin 3; azasetron; azatoxin; azatyrosine; baccatin III derivatives; balanol; BCR/ABL antagonists; benzochlorins; benzoylstaurosporine; beta lactam derivatives; beta-alethine; betaclamycin B; betulinic acid; bFGF inhibitor; bisantrene; bisaziridinylspermine; bisnafide; bistratene A; brefeldin A or its prodrug breflate; budotitane; buthionine sulfoximine; calcipotriol; calphostin C; camptothecin derivatives (e.g., irinotecan); carboxamide-amino-triazole; carboxyamidotriazole; CaRest M3; CARN 700; cartilage derived inhibitor; casein kinase inhibitors; castanospermine; cecropin B; cetrorelix; chlorins; chloroquinoxaline sulfonamide; cicaprost; cis-porphyrin; clarithromycin (e.g., BIAXIN®); clomifene analogues; clotrimazole; collismycin A; collismycin B; combretastatin A4, combretastatin analogues; conagenin; crambescidin 816; cryptophycin 8; cryptophycin A derivatives; curacin A; cyclopentanthraquinones; cycloplatam; cypemycin; cytolytic factor; cytostatin; dehydrodidemnin B; deslorelin; dexamethasone (e.g., DECADRON®); dexifosfamide; dexrazoxane; dexverapamil; didemnin B; didox; diethylnorspermine; dihydro-5-azacytidine; 9-dihydrotaxol; dioxamycin; diphenyl; docetaxel (e.g., TAXOTERE®); docosanol; doxifluridine; duocarmycin SA; ebselen; ecomustine; edelfosine; elemene; emitefur; epristeride; estrogen agonists; estrogen antagonists; exemestane (e.g., AROMASIN®); fadrozole; filgrastim; finasteride; flavopiridol (alvocidib); flezelastine; fluasterone; fluorodaunorunicin hydrochloride; forfenimex; formestane; fotemustine; gadolinium texaphyrin; gallium nitrate; galocitabine; ganciclovir; ganirelix; gelatinase inhibitors; glutathione inhibitors; hepsulfam; heregulin; hexamethylene bisacetamide;

hypericin; ibandronic acid; idoxifene; idramantone; ilomastat; imatinib mesylate (e.g., GLEEVEC®); imiquimod (e.g., ALDARA®), and other cytokine inducers; immunostimulant peptides; insulin-like growth factor-1 receptor inhibitor; interferon agonists; interferons such as interferon alpha (e.g., INTRON® A); pegylated interferon alfa-2b (e.g., PEGINTRON®); interleukins such as IL-2 (aldesleukin, e.g., PROLEUKIN®); iobenguane; iododoxorubicin; 4-ipomeanol; iroplact; irsogladine; isobengazole; isohomohalicondrin B; jasplakinolide; kahalalide F; lamellarin-N triacetate; leinamycin; lenograstim; lentinan sulfate; leptolstatin; leukemia inhibiting factor; leukocyte alpha interferon; leuprolide+estrogen+progesterone; leuprorelin; levamisole; linear polyamine analogue; lipophilic disaccharide peptide; lipophilic platinum compounds; lissoclinamide 7; lobaplatin; lombricine; lonidamine; loxoribine; lurtotecan; lutetium texaphyrin; lysofylline; lytic peptides; maitansine; mannostatin A; marimastat; maspin; matrilysin inhibitors; matrix metalloproteinase inhibitors; merbarone; meterelin; methioninase; metoclopramide; MIF inhibitor; mifepristone (e.g., MIFEPREX®); miltefosine; mirimostim; mitoguazone; mitolactol; mitonafide; mitotoxin fibroblast growth factor-saporin; mofarotene; human chorionic gonadotrophin; monophosphoryl lipid A+mycobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide (e.g., NILANDRON®); nisamycin; nitric oxide modulators; nitroxide antioxidants (e.g., tempol); nitrullyn; oblimersen (GENASENSE®); O6-benzylguanine; octreotide (e.g., SANDOSTATIN®); octreotide acetate (e.g., SANDOSTATIN LAR®); okicenone; oligonucleotides; onapristone; oracin; osaterone; oxaliplatin (e.g., ELOXATIN®); oxaunomycin; paclitaxel analogues; paclitaxel derivatives; palauamine; palmitoylrhizoxin; panaxytriol; panomifene; parabactin; pazelliptine; peldesine; pentosan polysulfate sodium; pentostatin (e.g., NIPENT®); pentrozole; perflubron; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum-triamine complex; propyl bis-acridone; prostaglandin J2; proteasome inhibitors; protein A-based immune modulator; protein kinase C inhibitors, including microalgal PKC inhibitors; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed (e.g., TOMUDEX®); ras farnesyl protein transferase inhibitors; ras inhibitors; ras-GAP inhibitor; retelliptine demethylated; rhenium ($^{186}$Re); rhizoxin; ribozymes; RII retinamide; rohitukine; romurtide; roquinimex; rubiginone B1; ruboxyl; saintopin; SarCNU; sarcophytol A; Sdi 1 mimetics; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; splenopentin; spongistatin 1; squalamine; steroids (e.g., prednisone, prednisolone); stipiamide; stromelysin inhibitors; sulfinosine; sulindac; superactive vasoactive intestinal peptide antagonist; suradista; suramin; swainsonine; tallimustine; tamoxifen, tamoxifen citrate (e.g., NOLVADEX®), tamoxifen methiodide; tauromustine; tazarotene; tellurapyrylium; telomerase inhibitors; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; titanocene bichloride; topsentin; translation inhibitors; tretinoin (all-trans retinoic acid, e.g., VESANOID®); triacetyluridine; turosteride; tyrosine kinase inhibitors; tyrphostins; UBC inhibitors; ubenimex; urogenital sinus-derived growth inhibitory factor; urokinase receptor antagonists; variolin B; velaresol; veramine; verdins; vinxaltine; vitaxin; zanoterone; and zilascorb.

Specific second active agents useful in the methods or compositions include, but are not limited to, rituximab, oblimersen (GENASENSE®), infliximab (REMICADE®), docetaxel, celecoxib, melphalan, dexamethasone (DECADRON®), steroids, gemcitabine, cisplatinum, temozolomide, etoposide, cyclophosphamide, temozolomide (TEMODAR®), carboplatin, procarbazine, gliadel, tamoxifen, topotecan, methotrexate, paclitaxel (TAXOL®), taxotere, 5-fluorouracil, leucovorin, irinotecan, capecitabine (XELODA®), CPT-11, interferon alpha, pegylated interferon alpha (e.g., PEGINTRON-A®), capecitabine, cisplatin, thiotepa, fludarabine, carboplatin, liposomal daunorubicin, cytarabine, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (DOXIL®), ganciclovir, adriamycin, estramustine sodium phosphate EMCYT®), sulindac, and etoposide.

In certain embodiments, the first active agent is SNS-595 and the second active agent is etoposide, daunomycin, actinomycin D, mitomycin C, cisplatin, carboplatin, premetrexed, methotrexate, cytarabine, 5-fluorouracil, wortmannin, geldanamycin, gemcitabine or a combination thereof.

In certain embodiments, the second active agent is an antileukemic nucleoside, such as cytarabine and/or decitabine and/or troxacitabine. In some embodiments, the nucleoside is cytarabine. In certain embodiments, cytarabine can be administered simultaneously or sequentially with SNS-595. In certain embodiments, SNS-595 and cytarabine are used in combination methods that may also include the use of one or more other therapies including, but not limited to, other anti-cancer agents, anti-emetics and the like. In other embodiments, the second active agent is a supportive care agent, such as an antiemetic agent or a myeloid growth factor. Specific antiemetic agents include, but are not limited to, phenothiazines, butyrophenones, benzodiazapines, corticosteroids, serotonin antagonists, cannabinoids, and NK1 receptor antagonists. Examples of phenothiazine antiemetic agents include, but are not limited to, prochlorperazine and trimethobenzamide. Examples of butyrophenone antiemetic agents include, but are not limited to, haloperidol. Examples of benzodiazapine antiemetic agents include, but are not limited to, lorazepam. Examples of corticosteroid antiemetic agents include, but are not limited to, dexamethasone. Examples of serotonin receptor (5-HT3 receptor) antagonist antiemetic agents include, but are not limited to, dolasetron mesylate (e.g., ANZEMET®), granisetron (e.g., KYTRIL®),), itasetron, ondansetron (e.g., ZOFRAN®), palonosetron (e.g., ALOXI®) ramosetron, tropisetron (e.g., NAVOBAN®), batanopride, dazopride, renzapride. Examples of cannabinoid antiemetic agents include, but are not limited to, dronabinol. Examples of NK1 receptor antagonists include, but are not limited to, aprepitant (e.g., EMEND®).).

Other supportive care agents include myeloid growth factors that stimulate erythropoiesis or other hematopoietic processes, such as epoetin alfa (e.g., EPOGEN®, PROCRIT®); G-CSF and recombinant forms such as filgrastim (e.g., NEUPOGEN®), pegfilgrastim (e.g., NEULASTA®), and lenofilgrastim; darbepoetin alfa (e.g., ARANESP®);

and GM-CSF and recombinant forms such as sargramostim (e.g., LEUKINE®) or molgramostim (e.g., LEUCOMAX®). Recombinant and mutated forms of GM-CSF can be prepared as described in U.S. Pat. Nos. 5,391,485; 5,393,870; and 5,229,496; the entireties of which are incorporated herein by reference. Recombinant and mutated forms of G-CSF can be prepared as described in U.S. Pat. Nos. 4,810,643; 4,999,291; 5,528,823; and 5,580,755; the entireties of which are incorporated herein by reference.

Other supportive care agents include chemoprotectant agents such as amifostine (e.g., ETHYOL®), dexrazoxane (e.g., ZINECARD®),), leucovorin (folinic acid), and mesna (e.g., MESNEX®); thrombopoeitic growth factors such as interleukin-11 (IL-11, oprelvekin, e.g., NEUMEGA®);); bisphosphonates such as pamidronate disodium (e.g., AREDIA®), etidronate disodium (e.g., DIDRONEL®) and zoledronic acid (e.g., ZOMETA®); and TNF antagonists, such as infliximab (e.g., REMICADE®).

In certain embodiments of the methods provided herein, use of a second active agent in combination with SNS-595 may be modified or delayed during or shortly following administration of SNS-595 as deemed appropriate by the practitioner of skill in the art. In certain embodiments, subjects being administered SNS-595 alone or in combination with other therapies may receive supportive care including antiemetics, myeloid growth factors, and transfusions of platelets, when appropriate.

In some embodiments, subjects being administered SNS-595 may be administered a growth factor as a second active agent according to the judgment of the practitioner of skill in the art. In some embodiments, provided is administration of SNS-595 in combination with erythropoietin or darbepoetin. Again, the method includes the use of these agents with the addition of others such as cytarabine. In certain embodiments, administration of erythropoietin or darbepoetin is delayed during administration of SNS-595, cytarabine or both. In certain embodiments, erythropoietin or darbepoetin is administered during administration of SNS-595, for instance when the subject presents anemia or severe anemia. In some embodiments, administration of prophylactic GM-CSF, sargramostim, molgramostim, G-CSF, filgrastim, or pegfilgrastim is delayed during one or more administrations of SNS-595. In certain embodiments, administration of prophylactic GM-CSF, sargramostim, molgramostim, G-CSF, filgrastim, or pegfilgrastim is permitted after administration of SNS-595, for instance, in a subject experiencing neutropenia or recurrent neutropenia. In certain embodiments, a myeloid growth factor may be administered in combination with SNS-595, for instance in a subject with a serious neutropenic complications, such as tissue infection, sepsis syndrome, or fungal infection, or at the discretion of the skilled practitioner.

In certain embodiments, administration of SNS-595 is performed in combination with one or more supportive care treatment(s) to mitigate or prevent tumor lysis syndrome or its component symptoms. Treatments suitable for preventing or mitigating TLS (or any of the symptoms thereof, including hyperkalemia, hyperphosphatemia, hyperuricemia, hypocalcemia, and acute renal failure), include, for example, allopurinol (e.g., Zyloprim®), rasburicase (e.g., Elitek®), and sodium polystyrene sulfonate (e.g., Kayexalate®). Leukapheresis may be performed, for example, up to 72 hours after the first treatment with SNS-595.

Doses and dosing regimens of SNS-595 together with other active moieties and combinations thereof should depend on the specific indication being treated, the age and condition of a patient, and the severity of adverse effects, and may be adjusted accordingly by those of skill in the art. Examples of conventional doses and dosing regimens for other active moieties can be found, for example, in *Physicians' Desk Reference*, and will require adaptation for use in the methods provided herein.

Methods of Treatment and Prevention

The methods provided herein encompass treating, preventing, or managing antecedent hematological disorders in a subject, for example, myelodysplastic syndromes, including refractory anemia (RA), RA with ringed sideroblasts (RARS), RA with excess blasts (RAEB), RAEB in transformation (RAEB-T), and CMML. In some embodiments, the myelodysplastic syndrome is refractory anemia (RA). In some embodiments, the myelodysplastic syndrome is refractory anemia with ringed sideroblasts (RARS). In some embodiments, the myelodysplastic syndrome is refractory anemia with excess blasts (RAEB). In some embodiments, the myelodysplastic syndrome is refractory anemia in transformation (RAEB-T). In some embodiments, the myelodysplastic syndrome is CMML.

In certain embodiments, myelodysplastic syndrome or MDS is characterized by one or more of the following: ineffective blood cell production, progressive cytopenias, risk of progression to acute leukemia or cellular marrow with impaired morphology and maturation (dysmyelopoiesis). The symptoms associated with MDS include, but are not limited to, anemia, thrombocytopenia, neutropenia, cytopenia, bicytopenia (two deficient cell types), and pancytopenia (three deficient cell types).

In certain embodiments, the method of treating, preventing, or managing MDS comprises the step of administering to the subject a therapeutically effective amount of an enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595). In certain embodiments, the method of treating MDS encompasses administration of the compound after the onset of symptoms of MDS. In certain embodiments, the method of preventing MDS encompasses administration prior to the onset of symptoms, particularly to patients at risk of MDS.

Further provided are methods of treating or preventing patients with primary and secondary MDS. The methods further encompass treating patients who have been previously treated for MDS, as well as those who have not previously been treated for MDS. Because patients with MDS have heterogeneous clinical manifestations and varying clinical outcomes, it has become apparent that staging the patients according to their prognosis and approaching therapy depending on the severity and stage is necessary. The methods and compositions provided herein are useful in various stages of treatments for patients with one or more types of MDS including, but not limited to, refractory anemia (RA), RA with ringed sideroblasts (RARS), RA with excess blasts (RAEB), RAEB in transformation (RAEB-T), or CMML. In one embodiment, the methods encompass treating patients diagnosed using the IPSS for MDS discussed above. Greenberg et al., *Blood* 1997 (89):2079-88.

In some embodiments, the methods comprise administering to the subject a therapeutically effective amount of SNS-595 in combination with a therapeutically effective amount of a second active agent. In some embodiments, the second active agent is a therapeutic antibody to a cancer antigen, a hematopoietic growth factor, a cytokine, an anti-cancer agent, an antibiotic, a cox-2 inhibitor, an immunomodulatory agent, an immunosuppressive agent, a corticosteroid, or a pharmacologically active mutant or derivative thereof. In other embodiments, the second active agent is an alkylating agent, an anti-neoplastic antibiotic, an anti-metabolite, a platinum coordination complex, a topoisomerase II inhibitor or poison, a CDK inhibitor, an aurora kinase inhibitor, or radiation. In other embodiments, the second active agent is etoposide, daunomycin, actinomycin D, mitomycin C, cisplatin, carboplatin, premetrexed, methotrexate, cytarabine, 5-Fu, wortmannin, geldanamycin, gemcitabine or a combination thereof. In a particular embodiment, the second active agent is cytarabine, which may be administered as cytarabine (e.g., Cytosar®), cytarabine liposomal (e.g., DepoCyt®), cytarabine ocfosfate, or other formulations of the active moiety.

In some embodiments, the methods provided herein encompass treating preventing or managing CMML in a subject. The methods comprise the step of administering to the subject an amount of SNS-595 effective to treat, prevent or manage CMML. In some embodiments, the methods comprise the step of administering to the subject SNS-595 in combination with a second active agent in amounts effective to treat, prevent or manage CMML. In a particular embodiment, the second active agent is cytarabine.

5.1.1 Subjects

In certain embodiments of the methods provided herein, the subject is an animal, preferably a mammal, more preferably a non-human primate. In particular embodiments, the subject is a human. The subject can be a male or female subject.

Particularly, subjects for the methods provided herein include patients suffering from antecedent hematological disorders, such as myelofibrosis, aplastic anemia, paroxysmal nocturnal hemoglobinuria, polycythemia vera, or myelodysplastic syndrome. The methods are particularly useful in the treatment of subjects afflicted with a myelodysplastic syndrome, including the disorders: refractory anemia (RA); refractory anemia with ring sideroblasts (RARS); refractory anemia with excess of blasts (RAEB); and CMML. In a particular embodiment, the subject suffers from CMML. In certain embodiments, CMML is refractory to and/or relapsed from prior therapy.

In some embodiments, the subject is treated according to the methods provided herein following a diagnosis of MDS according to any diagnostic criteria known to the skilled practitioner of the art. In some embodiments, the subject has been diagnosed with MDS according to the French-American-British (FAB) classification system. In a particular embodiment, the subject has been diagnosed with CMML under the FAB classification system. In some embodiments, the subject has been diagnosed with MDS according to the WHO proposed system of MDS classification. In some embodiments, the subject has been determined to be at risk for MDS according to the International Prognostic Scoring System (IPSS) for myelodysplastic syndrome. In a particular embodiment, the subject has a score of INT-2 or higher according to the IPSS scoring system.

In certain embodiments, the methods provided herein encompass the treatment of subjects who have not been previously treated for leukemia. In some embodiments, the subject has not undergone allogeneic bone marrow transplantation. In some embodiments, the subject has not undergone a stem cell transplantation. In some embodiments, the subject has not received hydroxyurea treatment. In some embodiments, the subject has not been treated with any investigational products for leukemia. In some embodiments, the subject has not been treated with systemic glucocorticoids.

In other embodiments, the methods encompass treating subjects who have been previously treated or are currently being treated for leukemia. For example, the subject may have been previously treated or are currently being treated with a standard treatment regimen for leukemia. In some embodiments, the subject has undergone autologous bone marrow transplantation or stem cell transplantation. In some embodiments, the bone marrow or stem cell transplantation occurred at least 3 months prior to treatment according to the methods provided herein. In some embodiments, the subject has undergone hydroxyurea treatment. In some embodiments, the hydroxyurea treatment occurred no later than 24 hours prior to treatment according to the methods provided herein. In some embodiments, the subject has undergone treatment with one or more of the following drugs: 5-azacytidine (Vidaza®), decitabine and lenalidomide (Revlimid®). In some embodiments, the subject has undergone prior induction or consolidation therapy with cytarabine. In some embodiments, the subject has undergone treatment with systemic glucocorticosteroids. In some embodiments, the glucocorticosteroid treatment occurred no later 24 hours prior to treatment according to the methods described herein. In other embodiments, the methods encompass treating subjects who have been previously treated for cancer, but are non-responsive (i.e., their conditions may be refractory and/or resistant) to standard therapies. For example, the subject may have been treated with an anticancer agent such as alemtuzumab; azacitabine; bortezomib; cyclophosphamide; cytarabine; decitabine; dexamethasone; doxorubicin; pegylated doxorubicin; liposomal doxorubicin; fludarabine; galiximab; lenalinomide; melphalan; prednisone; rituximab; thalidomide; or vincristine, or with a combination of anticancer agents such as fludarabine and alemtuzumab; fludarabine and cyclophosphamide; fludarabine, cyclophosphamide, and rituximab; fludarabine and rituximab; cyclophosphamide, vincristine, and prednisone; cyclophosphamide, vincristine, prednisone, and rituximab; melphalan and prednisone; melphalan, prednisone and thalidomide; or other combinations of such agents. The subject may have been treated with any standard leukemia treatment regimen known to the practitioner of skill in the art.

In some embodiments, the subject has not previously undergone treatment with SNS-595. In some embodiments, the subject has not previously undergone treatment with cytarabine. In some embodiments, the subject has not previously undergone treatment with SNS-595 in combination with a second active agent. In some embodiments, the subject has not previously undergone treatment with SNS-595 in combination with cytarabine. In other embodiments, the subject has previously undergone treatment with SNS-595. In some embodiments, the subject has previously undergone treatment with cytarabine. In some embodiments, the subject has previously undergone treatment with SNS-595 in combination with a second active agent. In some embodiments, the subject has previously undergone treatment with SNS-595 in combination with cytarabine.

Also encompassed are methods of treating a subject regardless of the subject's age, although some diseases or disorders are more common in certain age groups. In some embodiments, the subject is at least 18 years old. In some embodiments, the subject is more than 18, 25, 35, 40, 45, 50, 55, 65, 70, 75, 80 or 85 years old. In one embodiment, the subject is more than 80 years old. In other embodiments, the subject is less than 65 years old. In some embodiments, the subject is less than 18 years old. In some embodiments, the subject is less than 18, 15, 12, 10, 9, 8 or 7 years old.

In some embodiments, the methods find use in subjects at least 50 years of age, although younger subjects could benefit from the method as well. In other embodiments, the subjects are at least 55, at least 60, at least 65, and at least 70 years of age. In another embodiment, the subjects have adverse cytogenetics. "Adverse cytogenetics" is defined as any nondiploid karyotype, or greater than or equal to 3 chromosomal abnormalities. In another embodiment, the subjects are at least 60 years of age and have adverse cytogenetics. In another embodiment, the subjects are 60-65 years of age and have adverse cytogenetics. In another embodiment, the subjects are 65-70 years of age and have adverse cytogenetics. In some embodiments, subjects in this paragraph are administered a low dose of cytarabine as described herein.

In certain embodiments, the subject treated has no history of myocardial infarction within three months of treatment according to the methods provided herein. In some embodiments, the subject has no history of cerebrovascular accident or transient ischemic attack within three months of treatment according to the methods provided herein. In some embodiments, the subject has suffered no thromboembolic event, including deep vein thrombosis or pulmonary embolus, within 28 days of treatment according to the methods provided herein. In other embodiments, the subject has not experienced or is not experiencing uncontrolled disseminated intravascular coagulation.

Because subjects with antecedent hematologic disorders, such as MDS, have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapies that can be effectively used to treat an individual subject according to the invention.

5.1.2 Combination Therapy with a Second Active Agent

In certain embodiments, the methods provided herein comprise administering SNS-595 in combination with one or more second active agents, and/or in combination with radiation therapy, blood transfusions, or surgery. The administration of SNS-595 and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., *Physicians' Desk Reference*, 1755-1760 (56$^{th}$ ed., 2002).

In one embodiment, the second active agent is administered intravenously or subcutaneously and once or twice daily in an amount of from about 1 to about 1,500 mg/m$^2$, from about 5 to about 1,500 mg/m$^2$, from about 1 to about 1,000 mg, from about 5 to about 500 mg, from about 10 to about 375 mg, or from about 50 to about 200 mg.

The second active agent may be administered simultaneously, at essentially the same time, or sequentially with SNS-595. If such administration is conducted sequentially, second active agent may be administered before or after administration of SNS-595. In some embodiments, the second active agent is administered before administration of SNS-595. In some embodiments, the second active agent is administered simultaneously with administration of SNS-595. In some embodiments, the second active agent is administered after the administration of SNS-595. SNS-595 and the second active agent need not be administered by means of the same vehicle. In some embodiments, the second active agent and SNS-595 are administered in different vehicles. In embodiments of the methods described herein where delivery of SNS-595 and the second active agent are both by an intravenous route of administration, administration of each component of the combination need not be administered in the same IV line. In some embodiments, SNS-595 is administered in a different IV line than the second active agent. The second active agent may be administered one or more times, and the number of administrations of each component of the combination may be the same or different. In addition, SNS-595 and the second active agent need not be administered at the same site.

In other embodiments, provided herein are methods of treating, preventing and/or managing antecedent hematologic disorders, which comprise administering SNS-595 in conjunction with (e.g., before, during, or after) conventional therapy including, but not limited to, surgery, immunotherapy, biological therapy, radiation therapy, or other non-drug based therapy presently used to treat, prevent or manage cancer. Without being limited by theory, it is believed that SNS-595 may provide additive or synergistic effects when given concurrently with other anti-cancer therapy.

In one embodiment, SNS-595 can be administered in an amount of from about 1 to about 150 mg/m$^2$, about 1 to about 120 mg/m$^2$, about 1 to about 100 mg/m$^2$, about 1 to about 75 mg/m$^2$, about 1 to about 60 mg/m$^2$, about 1 to about 50 mg/m$^2$, alone, or in combination with a second active agent disclosed herein, prior to, during, or after the use of conventional therapy. In another specific embodiment, SNS-595 is administered at a dose of about 5 to about 50 mg/m$^2$ or about 10 to about 40 mg/m$^2$, or about 10 to about 90 mg/m$^2$.

In another embodiment, the methods provided herein comprise: a) administering to a patient in need thereof, a dose of about 1-150 mg/m$^2$ of SNS-595 and b) administering a therapeutically effective amount of a supportive care agent. Such support care agents are known in the art, for example, see, U.S. Application Publication No. 2006/0025437, which is incorporated by reference in its entirety.

In certain embodiments, the combination dosing of SNS-595 and cytarabine is used together as well with supportive care agents or other auxillary therapies. While not intending to be bound by any particular theory of operation, it is believed that SNS-595 and cytarabine can act synergistically in the methods provided herein. Exemplary dosing schedules for the combination dosing of SNS-595 and cytarabine are provided below.

Pharmaceutical Compositions and Dosage Forms

The methods provided herein use pharmaceutical compositions containing SNS-595 and pharmaceutically acceptable carriers, such as diluents or adjuvants, or in combination with other active ingredient, such as another anti-cancer agent. In clinical practice SNS-595 may be administered by any conventional route, including but not limited to orally, parenterally, rectally or by inhalation (e.g., in the form of aerosols). In one embodiment, SNS-595 is administered by an IV injection.

The compositions for parenteral administration can be emulsions or sterile solutions. Use may be made, as solvent or vehicle, of propylene glycol, a polyethylene glycol, vegetable oils, in particular olive oil, or injectable organic esters, for example, ethyl oleate. These compositions can also contain adjuvants, in particular wetting, isotonizing, emulsifying, dispersing and stabilizing agents. Sterilization can be carried out in several ways, for example, using a bacteriological filter, by radiation or by heating. They can also be prepared in the form of sterile solid compositions which can be dissolved at the time of use in sterile water or any other injectable sterile medium.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

Pharmaceutical compositions can be used in the preparation of individual, single unit dosage forms. Pharmaceutical compositions and dosage forms comprise SNS-595 and one or more excipients.

Pharmaceutical compositions and dosage forms can also comprise one or more additional active ingredients. Examples of optional second, or additional, active ingredients are disclosed herein.

In certain embodiments, a composition provided herein is a pharmaceutical composition or a single unit dosage form. Pharmaceutical compositions and single unit dosage forms provided herein comprise a prophylactically or therapeutically effective amount of SNS-595, and typically one or more pharmaceutically acceptable carriers or excipients. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In certain embodiments, water is a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in *Remington: The Science and Practice of Pharmacy*, 21st edition, Lippincott, Williams and Wilkins, Baltimore, Md. (2005), the contents of which are hereby incorporated by reference in their entirety.

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Further provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, powders and the like. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In one embodiment, the pharmaceutical compositions or single unit dosage forms are sterile and in suitable form for administration to a subject, such as a mammalian subject, such an animal subject, or in particular a human subject.

A pharmaceutical composition provided herein is formulated to be compatible with its intended route of administration. Examples of routes of administration include, but are not limited to, parenteral, e.g., intravenous, intradermal, subcutaneous, intramuscular, subcutaneous, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, intranasal or topical administration to human beings. In one embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Examples of dosage forms include, but are not limited to: liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of disease may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., *Remington: The Science and Practice of Pharmacy*, referenced hereinabove.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms provided herein comprise SNS-595 within the range of about 1 mg to about 150 mg per vial. Particular dosage forms provided herein have about 1, 3, 6, 9, 10, 12, 13.5, 15, 18, 19, 21, 24, 25, 27, 30, 38, 45, 50, 60, 63, 70, 75, 80, 85, 90, 95, 100, 105, 110, 115, 120, 125, 130, 135, 140, 145 or 150 mg of SNS-595 per vial.

5.5.1 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of active ingredients. See, e.g., U.S. Pat. No. 5,134,127, which is incorporated herein by reference.

5.6 Exemplary Dosages

The methods of treating, preventing or managing antecedent hematologic disorders, such as MDS, that are provided herein comprise administering to a patient SNS-595, alone or in combination with a second active agent. Doses of SNS-595 (and other agents) may be defined on the basis of body surface area. Body surface area (BSA) calculations can be calculated, for example, by means of the Mosteller formula wherein:

$$BSA(m^2) = \text{square root of } [(height(cm) \times weight(kg)/3600].$$

The administered dose of SNS-595 (and other agents) can be expressed in units other than as mg/m². For example, doses can be expressed as mg/kg. One of ordinary skill in the art would readily know how to convert doses from mg/m² to mg/kg for a human subject, given the height and weight of the subject.

In one embodiment, SNS-595 can be administered orally or intravenously and in single or divided daily doses in an amount of about 1 mg/m² to about 150 mg/m² (i.e. about 1-150 mg/m²). Certain exemplary doses per day include about 10, 15, 18, 21, 24, 25, 27, 30, 35, 40, 45, 48, 50, 55, 60, 63, 70, 72, 75, 80, 85, 90, 95, 100, 105, 110, 115, 120, 125, 130, 135, 140, 145 or 150 mg/m².

In another embodiment, the methods of comprise administering a dose of about 10-120 mg/m² of SNS-595. In another embodiment, the methods of comprise administering a dose of about 10-110 mg/m² of SNS-595. In another embodiment, the dose is about 15-100 mg/m². In another embodiment, the dose is about 30-75 mg/m². In another embodiment, the dose is about 40-80 mg/m². In another embodiment, the dose is about 50-90 mg/m². In another embodiment, the dose is about 15-80 mg/m².

In another embodiment the dose of SNS-595 is about 20-30 mg/m². In another embodiment the dose is about 25-35 mg/m². In another embodiment the dose is about 40-50 mg/m². In another embodiment the dose is about 45-55 mg/m². In another embodiment the dose is about 50-60 mg/m². In another embodiment the dose is about 55-65 mg/m². In another embodiment the dose is about 60-70 mg/m². In another embodiment the dose is about 65-75 mg/m². In another embodiment the dose is about 70-80 mg/m². In another embodiment the dose is about 75-85 mg/m². In another embodiment the dose is about 80-90 mg/m². In another embodiment the dose is about 85-95 mg/m². In another embodiment the dose is about 90-100 mg/m². In another embodiment the dose is about 100-110 mg/m². In another embodiment the dose is about 110-120 mg/m². In another embodiment the dose is about 120-130 mg/m². In another embodiment the dose is about 130-140 mg/m². In another embodiment the dose is about 140-150 mg/m².

In another embodiment, the dose of SNS-595 is 15 mg/m², 16 mg/m², 17 mg/m², 18 mg/m², 19 mg/m², 20 mg/m², 21 mg/m², 22 mg/m², 23 mg/m², 24 mg/m², 25 mg/m², 26 mg/m², 27 mg/m², 28 mg/m², 29 mg/m², 30 mg/m², 31 mg/m², 32 mg/m², 33 mg/m², 34 mg/m², 35 mg/m², 36 mg/m², 37 mg/m², 38 mg/m², 39 mg/m², 40 mg/m², 41 mg/m², 42 mg/m², 43 mg/m², 44 mg/m², 45 mg/m², 46 mg/m², 47 mg/m², 48 mg/m², 49 mg/m², 50 mg/m², 51 mg/m², 52 mg/m², 53 mg/m², 54 mg/m², 55 mg/m², 56 mg/m², 57 mg/m², 58 mg/m², 59 mg/m², 60 mg/m², 61 mg/m², 62 mg/m², 63 mg/m², 64 mg/m², 65 mg/m², 66 mg/m², 67 mg/m², 68 mg/m², 69 mg/m², 70 mg/m², 71 mg/m², 72 mg/m², 73 mg/m², 74 mg/m², 75 mg/m², 76 mg/m², 77 mg/m², 78 mg/m², 79 mg/m², 80 mg/m², 81 mg/m², 82 mg/m², 83 mg/m², 84 mg/m², 85 mg/m², 86 mg/m², 87 mg/m², 88 mg/m², 89 mg/m², 90 mg/m², 91 mg/m², 92 mg/m², 93 mg/m², 94 mg/m², 95 mg/m², 96 mg/m², 97 mg/m², 98 mg/m², 99 mg/m², 100 m g/m², 110 mg/m², 111 mg/m², 112 mg/m², 113 mg/m², 114 mg/m², 115 mg/m², 116 mg/m², 117 mg/m², 118 mg/m², 119 mg/m², 120 mg/m², 121 mg/m², 122 mg/m², 123 mg/m², 124 mg/m², 125 mg/m², 126 mg/m², 127 mg/m², 128 mg/m², 129 mg/m², 130 mg/m², 131 mg/m², 132 mg/m², 133 mg/m², 134 mg/m², 135 mg/m², 136 mg/m², 137 mg/m², 138 mg/m², 139 mg/m², 140 mg/m², 141 mg/m², 142 mg/m², 143 mg/m², 144 mg/m², 145 mg/m², 146 mg/m², 147 mg/m², 148 mg/m², 149 mg/m², or 150 mg/m².

The administered dose of SNS-595 can be delivered as a single dose (e.g. a single bolus IV injection) or over a 24-hour period (e.g., continuous infusion over time or divided bolus doses over time) and is repeated until the patient experiences stable disease or regression, or until the patient experiences disease progression or unacceptable toxicity. Stable disease or lack thereof is determined by methods known in the art, such as evaluation of patient symptoms, physical examination and other commonly accepted evaluation modalities.

In certain embodiments, SNS-595 is cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

In one embodiment, the methods provided herein comprise: i) administering a dose of about 10-120 mg/m² of SNS-595 to a mammal; ii) waiting a period of at least one day where the mammal is not administered any SNS-595; iii) administering another dose of about 10-120 mg/m² of SNS-595 to the mammal. Optionally, the method comprises repeating steps ii)-iii) once, twice, or a plurality of times.

In one embodiment, the methods provided herein comprise: i) administering a dose of about 10-90 mg/m² of SNS-595 to a mammal; ii) waiting a period of at least one day where the mammal is not administered any SNS-595; iii) administering another dose of about 10-90 mg/m$^2$ of SNS-595 to the mammal. Optionally, the method comprises repeating steps ii)-iii) once, twice, or a plurality of times.

In one embodiment, the methods provided herein comprise: i) administering a dose of about 10-40 mg/m$^2$ of SNS-595 to a mammal; ii) waiting a period of at least one day where the mammal is not administered any SNS-595; iii) administering another dose of about 10-40 mg/m$^2$ of SNS-595 to the mammal. Optionally, the method comprises repeating steps ii)-iii) once, twice, or a plurality of times.

In another embodiment, the dose of SNS-595 is about 10-150 mg/m$^2$ once per week. In another embodiment, the dose is about 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 72 mg/m$^2$, 75 mg/m$^2$, 80 mg/m$^2$, 85 mg/m$^2$, 90 mg/m$^2$, 95 mg/m$^2$, 100 mg/m$^2$, 105 mg/m$^2$, 110 mg/m$^2$, 115 mg/m$^2$, or 120 mg/m$^2$, once per week. In another embodiment, the dose is about 72 mg/m$^2$ once per week.

In another embodiment, the dose of SNS-595 is about 1-75 mg/m$^2$ twice per week. In another embodiment, the dose is about 5 mg/m$^2$, 7.5 mg/m$^2$, 10 mg/m$^2$, 12.5 mg/m$^2$, 15 mg/m$^2$, 17.5 mg/m$^2$, 20 mg/m$^2$, 22.5 mg/m$^2$, 25 mg/m$^2$, 27.5 mg/m$^2$, 30 mg/m$^2$, 32.5 mg/m$^2$, 35 mg/m$^2$, 37.5 mg/m$^2$, 40 mg/m$^2$, 42.5 mg/m$^2$, 45 mg/m$^2$, 47.5 mg/m$^2$, 50 mg/m$^2$, 52.5 mg/m$^2$, 55 mg/m$^2$, 57.5 mg/m$^2$, or 60 mg/m$^2$, twice per week. In another embodiment, the dose is about 40 mg/m$^2$ twice per week.

5.1.3 Exemplary Dosages:
Combination Dosing of SNS-595 and Cytarabine
In certain embodiments, the methods provided herein comprise administering SNS-595 in combination with cytarabine. Cytarabine can be administered either prior to, concurrently with, or subsequent to administration of SNS-595. In some embodiments, cytarabine can be administered subcutaneously or intravenously. In certain embodiments, cytarabine is administered subcutaneously. In certain embodiments, cytarabine is administered intravenously. In one embodiment, the dose of cytarabine is about 5 mg/m$^2$ to about 1500 mg/m$^2$, about 5 mg/m$^2$ to about 50 mg/m$^2$, about 25 mg/m$^2$ to 1000 mg/m$^2$, 50 mg/m$^2$ to 600 mg/m$^2$ and 200 to 400 mg/m$^2$. In another embodiment, the dose of cytarabine is about 200 mg/m$^2$, 300 mg/m$^2$ or 400 mg/m$^2$. In another embodiment, the dose of cytarabine is about 400 mg/m$^2$. Cytarabine can be administered continuously, by bolus injection, or by divided bolus injections over a particular time period such as, for example, one day.

In another embodiment the dose of cytarabine is about 50-100 mg/m$^2$. In another embodiment the dose of cytarabine is about 100-150 mg/m$^2$. In another embodiment the dose of cytarabine is about 150-200 mg/m$^2$. In another embodiment the dose of cytarabine is about 200-250 mg/m$^2$. In another embodiment the dose of cytarabine is about 250-300 mg/m$^2$. In another embodiment the dose of cytarabine is about 350-400 mg/m$^2$. In another embodiment the dose of cytarabine is about 400-450 mg/m$^2$. In another embodiment the dose of cytarabine is about 450-500 mg/m$^2$. In another embodiment the dose of cytarabine is about 500-550 mg/m$^2$. In another embodiment the dose of cytarabine is about 550-600 mg/m$^2$.

In some embodiments, treatment of antecedent hematologic disorders in a subject in need thereof with a combination of SNS-595 and cytarabine comprises dosing the subject with about 1-150 mg/m$^2$ of SNS-595 and about 100-500 mg/m$^2$ of cytarabine. In certain embodiments, the subject is dosed with 10 mg/m$^2$ SNS-595 and 400 mg/m$^2$ of cytarabine; 18 mg/m$^2$ SNS-595 and 400 mg/m$^2$ of cytarabine; 30 mg/m$^2$ SNS-595 and 400 mg/m$^2$ of cytarabine; 45 mg/m$^2$ SNS-595 and 400 mg/m$^2$ of cytarabine; 63 mg/m$^2$ SNS-595 and 400 mg/m$^2$ of cytarabine; 70 mg/m$^2$ SNS-595 and 400 mg/m$^2$ of cytarabine; 72 mg/m$^2$ SNS-595 and 400 mg/m$^2$ of cytarabine; 75 mg/m$^2$ SNS-595 and 400 mg/m$^2$ of cytarabine; 80 mg/m$^2$ SNS-595 and 400 mg/m$^2$ of cytarabine; 90 mg/m$^2$ SNS-595 and 400 mg/m$^2$ of cytarabine; 100 mg/m$^2$ SNS-595 and 400 mg/m$^2$ of cytarabine; 110 mg/m$^2$ SNS-595 and 400 mg/m$^2$ of cytarabine; 120 mg/m$^2$ SNS-595 and 400 mg/m$^2$ of cytarabine; 130 mg/m$^2$ SNS-595 and 400 mg/m$^2$ of cytarabine; 140 mg/m$^2$ SNS-595 and 400 mg/m$^2$ of cytarabine; or 150 mg/m$^2$ SNS-595 and 400 mg/m$^2$ of cytarabine. In some embodiments, the subject is dosed with about 10 mg/m$^2$ of SNS-595 and about 400 mg/m$^2$ of cytarabine. In some embodiments, the subject is dosed with about 20 mg/m$^2$ of SNS-595 and about 400 mg/m$^2$ of cytarabine. In some embodiments, the subject is dosed with about 30 mg/m$^2$ of SNS-595 and about 400 mg/m$^2$ of cytarabine. In some embodiments, the subject is dosed with about 45 mg/m$^2$ of SNS-595 and about 400 mg/m$^2$ of cytarabine. In some embodiments, the subject is dosed with about 60 mg/m$^2$ of SNS-595 and about 400 mg/m$^2$ of cytarabine. In some embodiments, the subject is dosed with about 70 mg/m$^2$ of SNS-595 and about 400 mg/m$^2$ of cytarabine. In some embodiments, the subject is dosed with about 72 mg/m$^2$ of SNS-595 and about 400 mg/m$^2$ of cytarabine. In some embodiments, the subject is dosed with about 75 mg/m$^2$ of SNS-595 and about 400 mg/m$^2$ of cytarabine. In some embodiments, the subject is dosed with about 80 mg/m$^2$ of SNS-595 and about 400 mg/m$^2$ of cytarabine. In some embodiments, the subject is dosed with about 90 mg/m$^2$ of SNS-595 and about 400 mg/m$^2$ of cytarabine. In some embodiments, the subject is dosed with about 100 mg/m$^2$ of SNS-595 and about 400 mg/m$^2$ of cytarabine. In some embodiments, the subject is dosed with about 110 mg/m$^2$ of SNS-595 and about 400 mg/m$^2$ of cytarabine. In some embodiments, the subject is dosed with about 120 mg/m$^2$ of SNS-595 and about 400 mg/m$^2$ of cytarabine. In some embodiments, the subject is dosed with about 130 mg/m$^2$ of SNS-595 and about 400 mg/m$^2$ of cytarabine. In some embodiments, the subject is dosed with about 140 mg/m$^2$ of SNS-595 and about 400 mg/m$^2$ of cytarabine. In some embodiments, the subject is dosed with about 150 mg/m$^2$ of SNS-595 and about 400 mg/m$^2$ of cytarabine.

In certain embodiments, the subject is dosed with 10 mg/m$^2$ SNS-595 and 200 mg/m$^2$ of cytarabine; 18 mg/m$^2$ SNS-595 and 200 mg/m$^2$ of cytarabine; 30 mg/m$^2$ SNS-595 and 200 mg/m$^2$ of cytarabine; 45 mg/m$^2$ SNS-595 and 200 mg/m$^2$ of cytarabine; 63 mg/m$^2$ SNS-595 and 200 mg/m$^2$ of cytarabine; 70 mg/m$^2$ SNS-595 and 200 mg/m$^2$ of cytarabine; 72 mg/m$^2$ SNS-595 and 200 mg/m$^2$ of cytarabine; 75 mg/m$^2$ SNS-595 and 200 mg/m$^2$ of cytarabine; 80 mg/m$^2$ SNS-595 and 200 mg/m$^2$ of cytarabine; 90 mg/m$^2$ SNS-595 and 200 mg/m$^2$ of cytarabine; 100 mg/m$^2$ SNS-595 and 200 mg/m$^2$ of cytarabine; 100 mg/m$^2$ SNS-595 and 200 mg/m$^2$ of cytarabine; 110 mg/m$^2$ SNS-595 and 200 mg/m$^2$ of cytarabine; 120 mg/m$^2$ SNS-595 and 200 mg/m$^2$ of cytarabine; 130 mg/m$^2$ SNS-595 and 200 mg/m$^2$ of cytarabine; 140 mg/m$^2$ SNS-595 and 200 mg/m$^2$ of cytarabine; or 150 mg/m$^2$ SNS-595 and 200 mg/m$^2$ of cytarabine. In some embodiments, the subject is dosed with about 10 mg/m$^2$ of SNS-595 and about 200 mg/m$^2$ of cytarabine. In some embodiments, the subject is dosed with about 20 mg/m$^2$ of SNS-595 and about 200 mg/m$^2$ of cytarabine. In some embodiments, the subject is dosed with about 30 mg/m$^2$ of SNS-595 and about 200 mg/m$^2$ of cytarabine. In some embodiments, the subject is dosed with about 45 mg/m$^2$ of SNS-595 and about 200 mg/m$^2$ of cytarabine. In some embodiments, the subject is dosed with about 60 mg/m$^2$ of SNS-595 and about 200 mg/m$^2$ of cytarabine. In some embodiments, the subject is dosed with about 70 mg/m$^2$ of SNS-595 and about 200 mg/m$^2$ of cytarabine. In some embodiments, the subject is dosed with about 72 mg/m$^2$ of SNS-595 and about 200 mg/m$^2$ of cytarabine. In some embodiments, the subject is dosed with about 75 mg/m$^2$ of SNS-595 and about 200 mg/m$^2$ of cytarabine. In some embodiments, the subject is dosed with about 80 mg/m$^2$ of SNS-595 and about 200 mg/m$^2$ of cytarabine. In some embodiments, the subject is dosed with about 90 mg/m$^2$ of SNS-595 and about 200 mg/m$^2$ of cytarabine. In some embodiments, the subject is dosed with about 100 mg/m$^2$ of SNS-595 and about 200 mg/m$^2$ of cytarabine. In some embodiments, the subject is dosed with about 110 mg/m$^2$ of SNS-595 and about 200 mg/m$^2$ of cytarabine. In some embodiments, the subject is dosed with about 120 mg/m$^2$ of SNS-595 and about 200 mg/m$^2$ of cytarabine. In some embodiments, the subject is dosed with about 130 mg/m$^2$ of SNS-595 and about 200 mg/m$^2$ of cytarabine. In some embodiments, the subject is dosed with about 140 mg/m$^2$ of SNS-595 and about 200 mg/m$^2$ of cytarabine. In some embodiments, the subject is dosed with about 150 mg/m$^2$ of SNS-595 and about 200 mg/m$^2$ of cytarabine.

In other embodiments, the exemplary combination dosages of SNS-595 and cytarabine provided herein comprise the total weekly dosage of SNS-595, and the total daily dosage of cytarabine, respectively. For example, where a subject treated by the methods provided herein with a combination dose of about 70 mg/m$^2$ of SNS-595 and about 400 mg/m$^2$ of cytarabine, the subject is treated a total weekly dose of about 70 mg/m$^2$ SNS-595, and a daily dose of about 400 mg/m$^2$ of cytarabine over the course of seven days.

In certain embodiments, the method of treating, preventing or managing an antecedent hematologic disorders in a subject in need thereof comprises administering a total dosage of about 10-120 mg/m$^2$ SNS-595, in combination with a continuous intravenous dose of about 50-600 mg/m$^2$/day cytarabine over a 5-day period, wherein the 5-day period comprises a treatment cycle. In some embodiments, the method comprises administering a total dosage of about 10-120 mg/m$^2$ SNS-595 in combination with a continuous intravenous dose of about 200-400 mg/m$^2$/day cytarabine over a 5-day period, wherein the 5-day period comprises a treatment cycle. In certain embodiments, the methods of treating, preventing or managing an antecedent hematologic disorder in a subject in need thereof comprise administering a total dosage of about 10-40 mg/m$^2$ SNS-595, in combination with a continuous intravenous dose of about 50-600 mg/m$^2$/day cytarabine over a 5-day period, wherein the 5-day period comprises a treatment cycle. In some embodiments, the method comprises administering a total dosage of about 20-40 mg/m$^2$ SNS-595 in combination with a continuous intravenous dose of about 200-400 mg/m$^2$/day cytarabine over a 5-day period, wherein the 5-day period comprises a treatment cycle. In some embodiments, the method comprises administering a total dosage of about 10, 20, 30 or 40 mg/m$^2$ SNS-595 in combination with a continuous intravenous dose of about 200, 300 or 400 mg/m$^2$/day cytarabine over a 5-day period, wherein the 5-day period comprises a treatment cycle. In some embodiments, the method comprises administering a total dosage of about 40-80 mg/m$^2$ SNS-595 in combination with a continuous intravenous dose of about 400 mg/m$^2$/day cytarabine over a 5-day period, wherein the 5-day period comprises a treatment cycle. In some embodiments, the method comprises administering a total dosage of about 70 mg/m$^2$ SNS-595 in combination with a continuous intravenous dose of about 400 mg/m$^2$/day cytarabine over a 5-day period, wherein the 5-day period comprises a treatment cycle. In some embodiments, the treatment cycle is repeated at least once. In some embodiments, the treatment cycle is repeated at least twice. In some embodiments, the treatment cycle is repeated at least three times. In some embodiments, the treatment cycle is repeated at least four times.

In certain embodiments, the methods of treating, preventing, or managing antecedent hematological disorders in a subject in need thereof comprises administering a total weekly amount of about 10-120 mg/m$^2$ SNS-595 in combination with a total daily amount of about 10-50 mg/m$^2$ cytarabine.

In one embodiment, the doses of cytarabine used are about 5-25 mg/m$^2$. Such doses are referred to herein as low dose cytarabine for use in certain antecedent hematologic disorders and in certain patient populations. In another embodiment the doses of cytarabine used are about 5-25 mg/m$^2$ twice a day. In another embodiment, the doses of cytarabine used are about 5-25 mg/m$^2$ twice a day for 10 days. In another embodiment the cytarabine is administered subcutaneously (SC). In another embodiment, the dose is about 10-20 mg/m$^2$ cytarabine twice a day. In another embodiment the cytarabine dose is about 10 mg/m$^2$ SC twice a day for 10 days. In another embodiment, the cytarabine dose is about 15 mg/m$^2$ SC twice a day for 10 days. In another embodiment, the cytarabine dose is about 20 mg/m$^2$ SC twice a day for 10 days.

In another embodiment, the dose of cytarabine is 10-40 mg/m$^2$ once a day. In another embodiment, the dose of cytarabine is 10-40 mg/m$^2$ once a day for 10 days. In another embodiment the dose is administered subcutaneously. In another embodiment, the dose is from 15-30 mg/m$^2$ cytarabine. In another embodiment the cytarabine dose is 20 mg/m$^2$ SC once per day. In another embodiment, the cytarabine dose is 20 mg/m$^2$ SC once per day for 10 days.

SNS-595 schedules that can be used in combination with cytarabine at a total daily cytarabine dose of 10-50 mg/m$^2$ (administered as a continuous infusion, single bolus, or divided boluses), include, for example, SNS-595 administered once per week for three weeks (Day 1, 8, and 15) and SNS-595 administered twice per week for two weeks (Days 1, 4, 8, and 11). In certain embodiments, doses of SNS-595 are about 10-90 mg/m$^2$ for the once a week for three weeks schedule and about 10-50 mg/m$^2$ for the twice per week for two weeks schedule. In one embodiment, the daily cytarabine doses are administered for 10 days starting on the same day as (i.e. within 24 hours of) the initiation of the SNS-595 dose.

Duration (interval) between repeated administrations of the schedules can range from about 1 week to 8 weeks after the end of the schedule (e.g., after Day 15 or Day 11 respectively). In another embodiment, the interval is from 3 weeks to 6 weeks. In another embodiment, the interval is from 4 weeks to 6 weeks. In another embodiment, the interval is measured from Day 21 or Day 14, for the once a week for three weeks and twice a week for two week schedules, respectively 5.1.4 Exemplary Dosing Schedules of SNS-595 and Cytarabine In the embodiments of the present invention, SNS-595 and cytarabine can be administered according to any schedule deemed suitable by a practitioner of skill in the art. Provided in this section are exemplary dosing schedules of SNS-595 in combination with cytarabine that can be practiced within the present invention.

In certain embodiments, SNS-595 and cytarabine are administered in cycles. In certain embodiments, SNS-595 and cytarabine are administered in at least one cycle. In certain embodiments, SNS-595 and cytarabine are administered in at least two cycles. In certain embodiments, SNS-595 and cytarabine are administered in at least three cycles. In certain embodiments, SNS-595 and cytarabine are administered in at least four cycles. In certain embodiments each cycle is at least 28 days.

In a cycle, SNS-595 and cytarabine are administered in combination. In certain embodiments, SNS-595 is administered in two doses three days apart, i.e. on days 1 and 4 of a cycle. In certain embodiments, cytarabine is administered by continuous intravenous infusion for five days. In certain embodiments, cytarabine is administered by continuous IV infusion on days 1 through 5 of a cycle. In certain embodiments, SNS-595 is administered in two doses three days apart, i.e. on days 1 and 4 of a cycle, and cytarabine is administered by continuous intravenous infusion for five days.

In certain embodiments, as discussed above, the initial dose of SNS-595 is administered before the administration of cytarabine. In certain embodiments, the initial dose of SNS-595 is administered immediately before the administration of cytarabine. In certain embodiments, administration of cytarabine is initiated 1, 2, 3, 4, 8, 12, 16, 24, or 32 hours following administration of SNS-595, for instance, 1, 2, 3, 4, 8, 12, 16, 24, or 32 hours following completion of the administration of SNS-595. In certain embodiments, administration of cytarabine is initiated about 8 hours following administration of SNS-595, for instance, 8 hours following administration of SNS-595.

In certain embodiments, provided is an assessment of the subject within a cycle. For instance, in certain embodiments, the subject is assessed for safety and/or efficacy of the therapy by any of the techniques described above. In certain embodiments, the subject is assessed 12-16 days following the initial administration of SNS-595 in the cycle (i.e. the subject is assessed on days 13, 14, 15, 16 or 17 of the cycle). In certain embodiments, the subject is assessed 14 days following initial administration of SNS-595 in the cycle (i.e. on day 15 of the cycle).

In certain embodiments, the subject is administered a following cycle of therapy based on an evaluation of the assessment by a practitioner of skill in the art. For instance, in certain embodiments, after a first cycle of therapy (Cycle 1), a subject can be administered a second cycle of therapy (Cycle 2) if bone marrow blasts are reduced with greater than 5% of blasts are observed in the marrow. In certain embodiments, therapy can be discontinued after the first cycle (Cycle 1) if the subject presents progressive disease.

In certain embodiments, after the second cycle of therapy (Cycle 2; Reinduction), a subject can be administered a third cycle of therapy (Cycle 3) if the subject presents morphologic complete remission ("CR"; >1000 neutrophils per microliter and >100,000 platelets per microliter of serum, and <5% bone marrow blasts). In certain embodiments, after a second cycle of therapy (Cycle 2), a subject can be administered a third cycle of therapy (Cycle 3) if the subject presents morphologic complete remission without platelet recovery ("CRp"; >1000 neutrophils per microliter, ≤100,000 platelets per microliter of serum, and <5% bone marrow blasts). In certain embodiments, after a second cycle of therapy (Cycle 2), a subject can be administered a third cycle of therapy (Cycle 3) if the subject presents morphologic complete remission without incomplete blood count recovery ("CRi"; ≤1000 neutrophils per microliter, ≤100,000 platelets per microliter of serum, and <5% bone marrow blasts). In certain embodiments, therapy can be discontinued after the first cycle (Cycle 1) if the subject presents progressive disease. In certain embodiments, therapy can be discontinued after the second cycle (Cycle 2) if the subject presents >5% bone marrow blasts.

In certain embodiments, after the third cycle of therapy (Cycle 3), a subject can be administered a fourth cycle of therapy (Cycle 4) if the subject presents peripheral blood CR (i.e. bone marrow need not be assessed). In certain embodiments, after a third cycle of therapy (Cycle 3), a subject can be administered a fourth cycle of therapy (Cycle 4) if the subject presents peripheral blood CRp (i.e. bone marrow need not be assessed). In certain embodiments, after a third cycle of therapy (Cycle 3), a subject can be administered a fourth cycle of therapy (Cycle 4) if the subject presents peripheral blood Cri (i.e. bone marrow need not be assessed). In certain embodiments, therapy can be discontinued after the third cycle (Cycle 3) if the subject presents progressive disease.

In certain embodiments, a subject can be administered Cycle 3 following Cycle 1. For instance, a subject proceeds from Cycle 1 to Cycle 3 if the subject presents CR, CRp, or CRi following Cycle 1.

In certain embodiments, Cycle 2 is initiated n more than 14 days following the assessment of Cycle 1 (Induction).

In certain embodiments, Cycle 3 is initiated 27 days to 83 days following the initiation of treatment in the previous Cycle (i.e. on day 28 to day 84 of the previous Cycle). As discussed above, in certain embodiments, Cycle 3 follows Cycle 1. In certain embodiments, Cycle 3 follows Cycle 2.

In certain embodiments, Cycle 4 is initiated at least 27 days following the initiation of treatment Cycle 3, i.e. on day 28 of Cycle 3.

In certain embodiments, the dose of SNS-595 is constant in each cycle of the therapy. In certain embodiments, the dose of cytarabine is constant in each cycle of the therapy. In certain embodiments, the dose of cytarabine is can be reduced from one Cycle to a second Cycle. For instance, in certain embodiments, in Cycle 1 cytarabine can be administered at 400 mg/m$^2$ while in Cycles 2-4 cytarabine can be administered at 200 mg/m$^2$. In certain embodiments, in Cycles 1-2 cytarabine can be administered at 400 mg/m$^2$ while in Cycles 2-4 cytarabine can be administered at 200 mg/m$^2$. In certain embodiments, in Cycles 1-3 cytarabine can be administered at 400 mg/m$^2$ while in Cycle 4 cytarabine can be administered at 200 mg/m$^2$. In certain embodiments, in Cycles 1-4 cytarabine can be administered at 400 mg/m$^2$. Such dose reductions are administered according to the judgment of a practitioner of skill in the art, for instance, if a subject presents one or more dose limiting toxicities described herein.

In certain embodiments, therapy can continue beyond Cycle 4 according to the assessment described above. Patients can continue to be monitored for remission according to the assessment following therapy according to the judgment of the practitioner of skill.

6. EXAMPLES

Certain embodiments of the invention are illustrated by the following non-limiting examples.

Example 1

Pharmaceutical Composition Suitable for Injection or Intravenous Infusion

Acidic compositions (<pH 4) provided the appropriate balance of increased solubility of SNS-595 and desirable pharmaceutical properties (e.g., increased patient comfort by causing less irritation at the delivery site). An illustrative example of a suitable composition comprises: 10 mg SNS-595 per mL of aqueous solution of 4.5% sorbitol that is adjusted to pH 2.5 with methanesulfonic acid. One protocol for making such a solution includes the following for making a 100 mg/10 mL presentation: 100 mg of SNS-595 and 450 mg D-sorbitol are added to distilled water; the volume is brought up to a volume of 10 mL; and the pH of the resulting solution is adjusted to 2.5 with methanesulfonic acid. The resulting composition is also suitable for lyophilization. The lyophilized form is then reconstituted with sterile water to the appropriate concentration prior to use.

Example 2

Clinical Study: Treatment with SNS-595

A caucasian female patient (81 years old) with MDS that had transformed to refractory CMML was enrolled in this study. The patient was diagnosed about 26 months prior to the study and was given 8 cycles of azacitadine (Vidaza®) about 10 months prior to the study. She was then treated with mitoxantrone+VP16 for 1 cycle, about 4 months prior to the study. The disease had progressed to AML prior to treatment with SNS-595.

The treatment with SNS-595 was started at 72 mg/m$^2$ (once per week for three weeks, as slow IV push).

The patient had initial marrow blast count of 39%. The following observations were noted on days 15 and 35.

|  | Peripheral Blasts | White blood cell (WBC) count | Absolute neutrophil count (ANC) |
| --- | --- | --- | --- |
| Day 15 | No blasts | 600 | 94 |
| Around Day 35 | 33% | 16000 (was 7000 but patient had Necrotizing fasciitis (NF) infection) | 3139 |

The data demonstrates that, although the patient ultimately had progressive disease, the treatment showed clinical benefit with reduction in splenomegaly and blast counts.

Example 3

Clinical Study: Treatment with SNS-595

A black/African-American male patient (58 years old) with relapsed CMML (transformed to AML) was enrolled. The patient was diagnosed about 17 months prior to the study, was treated with 1 cycle of a Southwest Oncology Group (SWOG) regimen after diagnosis. He was given 4 cycles of azacitadine (Vidaza®) about 14 months prior to study and 1 cycle of decitabine, about 6 months before the study.

The treatment with SNS-595 was started at 50 mg/m$^2$ (twice a week, as slow IV push). The patient showed initial marrow at baseline 20% blasts.

Post Cycle 1: marrow showed 8% blasts
Post Cycle 2: marrow showed 1% with 4% circulating blasts.
Post Cycle 3: there was 8% circulating blasts.
Post Cycle 4: there was 12% circulating blasts.

At the time of undergoing treatment with third cycle of SNS-595, the patient's absolute neutrophil count (ANC) was 1600.

The data demonstrates that the treatment showed clinical benefit (i.e. hematological improvement) with reduction in blast counts.

Example 4

Clinical Study: Treatment of Acute Leukemia with SNS-595

The safety and efficacy of SNS-595 were investigated in two dose-escalating studies. As demonstrated below, SNS-595 provides good safety profiles and evidence of clinical activity as measured by complete responses (CR) and decreases in leukemic blasts in patients with advanced or refractory acute leukemias.

In the study, total of 49 patients were enrolled, Arm A (SNS-595 was administered as a weekly×3): 25 patients and Arm B (SNS-595 was administered twice weekly×2 bolus): 24 patients. Thirty-one patients were male and 18 patients female, with a median age of 65 years. Diagnoses included AML (43 patients), ALL (4 patients), and 1 patient each with acute lymphoblastic leukemia and acute biphenotypic leukemia. Most patients had relapsed/refractory leukemia from prior therapy (median 3 prior regimens (range 1-7)).

SNS-595 was administered as a slow IV push on days 1, 8, 15 (Arm A) or days 1, 4, 8, 11 (Arm B). Minimum cycle length was 42 days for Arm A and 39 days for Arm B, respectively. Additional cycles were permitted if patients achieved stable disease or better. The starting dose of SNS-595 was 18 mg/m$^2$ weekly on Arm A, and 9 mg/m$^2$ twice weekly on Arm B. The dose was escalated by cohort.

Pharmakokinetic analyses for SNS-595 were performed during cycle 1. Pre- and post-dose bone marrow aspirates were obtained from a subset of patients to assess biomarkers.

The results provided herein are for dose escalation to 90 mg/m$^2$/day on Arm A. Three dose-limiting toxicities (DLTs) were observed on Arm A-G4 myelosuppression at the 27 mg/m$^2$ weekly dose (also had progressive disease), prolonged myelosuppression at the 50 mg/m$^2$ weekly dose, and bowel obstruction at the 72 mg/m$^2$ weekly dose. Non-dose-limiting toxicities (non-DLTs) included nausea/vomiting and diarrhea; drug-related G3 & 4 events were limited to stomatitis (3 patients) and diarrhea (1 patient).

On Arm B, dose-limiting toxicity (DLT) of Grade (G) 3 mucositis was observed in 3 patients at the 50 mg/m$^2$ dose level. At 40 mg/m$^2$, two patients out of 11 exhibited G3 mucositis.

Blast reduction (>95%) and response was associated with time above a threshold concentration of SNS-595. Following administration of SNS-595, evidence of DNA-damage induced by SNS-595 was detected. Clinical activity—reductions in marrow blasts to ≤5%—was noted at doses at or above 50 mg/m$^2$ (5 patients in Arm A) and 40 mg/m$^2$ (1 patient in Arm B). Complete Responses (CR) have been observed at the 50 mg/m$^2$ dose level (Arm A, 1 patient) and at the 40 mg/m$^2$ level (Arm B, 1 patient). A third patient with AML and splenomegaly achieved partial response at the 50 mg/m$^2$ dose level (Arm B) and had G3 mucositis. In addition, 1 patient with AML and splenomegaly (at 72 mg/m², Arm A) achieved clinical benefit with reduction in splenomegaly and blast counts.

This study demonstrates that SNS-595 is well-tolerated in patients with advanced leukemias, with preliminary signs of clinical activity as measured by complete responses (CR) and decreases in leukemic blasts.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating a myelodysplastic syndrome comprising administering to a mammal in need thereof (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid from about 1 to about 150 mg/m² and a therapeutically effective amount of azacitidine.

2. The method of claim 1, wherein the myelodysplastic syndrome is characterized by ineffective blood cell production, progressive cytopenia, risk of progression to acute leukemia or cellular marrow with impaired morphology.

3. The method of claim 1, wherein the myelodysplastic syndrome is selected from group consisting of refractory anemia, refractory anemia with ringed sideroblasts, refractory anemia with excess blasts, refractory anemia with excess blasts in transformation, and chronic myelomonocytic leukemia.

4. The method of claim 1, wherein (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is administered at a dose of from about 10 to about 90 mg/m².

5. The method of claim 1, wherein (+)-1,4-dihydro-7-[(3S,4S)-3-methoxy-4-(methylamino)- 1-pyrrolidinyl]-4-oxo- 1-(2-thiazolyl)- 1,8-naphthyridine-3 -carboxylic acid is administered as an IV injection.

6. The method of claim 1, wherein the mammal is human.

* * * * *